(12) United States Patent
Love et al.

(10) Patent No.: US 11,207,006 B2
(45) Date of Patent: Dec. 28, 2021

(54) SYSTEMS, DEVICES, AND METHODS FOR ENERGY EFFICIENT ELECTRICAL DEVICE ACTIVATION

(71) Applicant: ABBOTT DIABETES CARE INC., Alameda, CA (US)

(72) Inventors: Michael R. Love, Pleasanton, CA (US); Gary A. Hayter, Oakland, CA (US); Lei He, Moraga, CA (US); Hung Dinh, San Leandro, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 378 days.

(21) Appl. No.: 16/201,688

(22) Filed: Nov. 27, 2018

(65) Prior Publication Data

US 2019/0142315 A1 May 16, 2019

Related U.S. Application Data

(63) Continuation of application No. 14/265,026, filed on Apr. 29, 2014, now Pat. No. 10,213,141.
(Continued)

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/0015* (2013.01); *A61B 5/1455* (2013.01); *A61B 5/14546* (2013.01); *A61B 5/14865* (2013.01); *A61B 5/6833* (2013.01); *A61B 5/6849* (2013.01); *A61B 2560/0209* (2013.01); *A61B 2560/0214* (2013.01); *A61B 2560/0271* (2013.01)

(58) Field of Classification Search
CPC . A61B 5/14532; A61B 5/6849; A61B 5/0015; A61B 5/1455; A61B 5/6833; A61B 5/14546; A61B 5/14865; A61B 2560/0209; A61B 2560/0214; A61B 2560/0271
See application file for complete search history.

(56) References Cited

U.S. PATENT DOCUMENTS

| | | |
|---|---|---|
| 4,545,382 A | 10/1985 | Higgins et al. |
| 4,711,245 A | 12/1987 | Higgins et al. |

(Continued)

FOREIGN PATENT DOCUMENTS

| | | |
|---|---|---|
| WO | WO 2005/074161 A1 | 8/2005 |
| WO | WO 2008/129532 A2 | 10/2008 |

(Continued)

OTHER PUBLICATIONS

JP, 2019-142804 Office Action, dated Sep. 2, 2020.
(Continued)

*Primary Examiner* — Eric F Winakur
*Assistant Examiner* — Abid A Mustansir
(74) *Attorney, Agent, or Firm* — One LLP

(57) ABSTRACT

Systems, devices, and methods are provided for changing the power state of a sensor control device in an in vivo analyte monitoring system in various manners, such as through the use of external stimuli (light, magnetics) and RF transmissions.

20 Claims, 23 Drawing Sheets

Related U.S. Application Data

(60) Provisional application No. 61/973,775, filed on Apr. 1, 2014, provisional application No. 61/896,578, filed on Oct. 28, 2013, provisional application No. 61/817,839, filed on Apr. 30, 2013.

(51) Int. Cl.
*A61B 5/1486* (2006.01)
*A61B 5/1455* (2006.01)

(56) References Cited

U.S. PATENT DOCUMENTS

| | | | |
|---|---|---|---|
| 5,262,035 A | 11/1993 | Gregg et al. |
| 5,262,305 A | 11/1993 | Heller et al. |
| 5,264,104 A | 11/1993 | Gregg et al. |
| 5,267,152 A | 11/1993 | Yang et al. |
| 5,320,715 A | 6/1994 | Berg |
| 5,356,786 A | 10/1994 | Heller et al. |
| 5,509,410 A | 4/1996 | Hill et al. |
| 5,543,326 A | 8/1996 | Heller et al. |
| 5,593,852 A | 1/1997 | Heller et al. |
| 5,601,435 A | 2/1997 | Quy |
| 5,628,890 A | 5/1997 | Carter et al. |
| 5,820,551 A | 10/1998 | Hill et al. |
| 5,822,715 A | 10/1998 | Worthington et al. |
| 5,899,855 A | 5/1999 | Brown |
| 5,918,603 A | 7/1999 | Brown |
| 6,071,391 A | 6/2000 | Gotoh et al. |
| 6,103,033 A | 8/2000 | Say et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Hsieh et al. |
| 6,144,837 A | 11/2000 | Quy |
| 6,161,095 A | 12/2000 | Brown |
| 6,175,752 B1 | 1/2001 | Say et al. |
| 6,270,455 B1 | 8/2001 | Brown |
| 6,284,478 B1 | 9/2001 | Heller et al. |
| 6,299,757 B1 | 10/2001 | Feldman et al. |
| 6,338,790 B1 | 1/2002 | Feldman et al. |
| 6,377,894 B1 | 4/2002 | Deweese et al. |
| 6,461,496 B1 | 10/2002 | Feldman et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,540,891 B1 | 4/2003 | Stewart et al. |
| 6,560,471 B1 | 5/2003 | Heller et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,616,819 B1 | 9/2003 | Liamos et al. |
| 6,618,934 B1 | 9/2003 | Feldman et al. |
| 6,650,471 B2 | 11/2003 | Doi |
| 6,654,625 B1 | 11/2003 | Say et al. |
| 6,676,816 B2 | 1/2004 | Mao et al. |
| 6,730,200 B1 | 5/2004 | Stewart et al. |
| 6,736,957 B1 | 5/2004 | Forrow et al. |
| 6,746,582 B2 | 6/2004 | Heller et al. |
| 6,749,740 B2 | 6/2004 | Liamos et al. |
| 6,764,581 B1 | 7/2004 | Forrow et al. |
| 6,773,671 B1 | 8/2004 | Lewis et al. |
| 6,881,551 B2 | 4/2005 | Heller et al. |
| 6,893,545 B2 | 5/2005 | Gotoh et al. |
| 6,932,892 B2 | 8/2005 | Chen et al. |
| 6,932,894 B2 | 8/2005 | Mao et al. |
| 6,942,518 B2 | 9/2005 | Liamos et al. |
| 7,041,468 B2 | 5/2006 | Drucker et al. |
| 7,167,818 B2 | 1/2007 | Brown |
| 7,291,497 B2 | 11/2007 | Holmes et al. |
| 7,299,082 B2 | 11/2007 | Feldman et al. |
| 7,418,285 B2 | 8/2008 | Ghesquiere et al. |
| 7,501,053 B2 | 3/2009 | Karinka et al. |
| 7,545,272 B2 | 6/2009 | Goodnow et al. |
| 7,722,536 B2 | 5/2010 | Goodnow |
| 7,749,740 B2 | 7/2010 | Eiteman et al. |
| 7,754,093 B2 | 7/2010 | Forrow et al. |
| 7,768,408 B2 | 8/2010 | Reggiardo et al. |
| 7,782,192 B2 | 8/2010 | Jeckelmann et al. |
| 7,801,582 B2 | 9/2010 | Peyser |
| 7,811,231 B2 | 10/2010 | Jin et al. |
| 7,866,026 B1 | 1/2011 | Wang et al. |
| 8,066,639 B2 | 11/2011 | Nelson et al. |
| 8,219,173 B2 | 7/2012 | Budiman et al. |
| 8,346,335 B2 | 1/2013 | Harper et al. |
| 8,372,351 B2 | 2/2013 | Ow-Wing |
| 8,435,682 B2 | 5/2013 | Heller |
| 8,497,777 B2 | 7/2013 | Harper |
| 8,514,086 B2 | 8/2013 | Harper et al. |
| 8,515,518 B2 | 8/2013 | Ouyang et al. |
| 8,595,607 B2 | 11/2013 | Nekoomaram et al. |
| 8,601,465 B2 | 12/2013 | Bernstein et al. |
| 8,764,657 B2 | 7/2014 | Curry et al. |
| 8,771,183 B2 | 7/2014 | Sloan |
| 8,815,154 B2 | 8/2014 | List et al. |
| 8,816,862 B2 | 8/2014 | Harper et al. |
| 8,828,330 B2 | 9/2014 | Galasso |
| 9,295,784 B2 | 3/2016 | Eggert et al. |
| 2004/0118704 A1 | 6/2004 | Wang et al. |
| 2004/0186365 A1 | 9/2004 | Jin et al. |
| 2005/0182306 A1 | 8/2005 | Sloan |
| 2005/0261556 A1* | 11/2005 | Such ................ A61B 5/0002 600/300 |
| 2006/0025662 A1 | 2/2006 | Buse et al. |
| 2006/0091006 A1 | 5/2006 | Wang et al. |
| 2006/0166629 A1 | 7/2006 | Reggiardo |
| 2006/0193375 A1 | 8/2006 | Lee |
| 2007/0056858 A1 | 3/2007 | Chen et al. |
| 2007/0068807 A1 | 3/2007 | Feldman et al. |
| 2007/0095661 A1 | 5/2007 | Wang et al. |
| 2007/0102649 A1 | 5/2007 | Colvin et al. |
| 2007/0108048 A1 | 5/2007 | Wang et al. |
| 2007/0199818 A1 | 8/2007 | Petyt et al. |
| 2007/0227911 A1 | 10/2007 | Wang et al. |
| 2007/0232877 A1 | 10/2007 | He |
| 2007/0233013 A1 | 10/2007 | Schoenberg |
| 2008/0064937 A1 | 3/2008 | McGarraugh et al. |
| 2008/0066305 A1 | 3/2008 | Wang et al. |
| 2008/0081977 A1 | 4/2008 | Hayter et al. |
| 2008/0102441 A1 | 5/2008 | Chen et al. |
| 2008/0119705 A1 | 5/2008 | Patel et al. |
| 2008/0129486 A1 | 6/2008 | Jeckelmann et al. |
| 2008/0148873 A1 | 6/2008 | Wang |
| 2008/0154101 A1 | 6/2008 | Jain et al. |
| 2008/0161666 A1 | 7/2008 | Feldman et al. |
| 2008/0255434 A1 | 10/2008 | Hayter et al. |
| 2008/0255437 A1 | 10/2008 | Hayter |
| 2008/0255808 A1 | 10/2008 | Hayter |
| 2008/0256048 A1 | 10/2008 | Hayter |
| 2008/0267823 A1 | 10/2008 | Wang et al. |
| 2008/0281179 A1 | 11/2008 | Fennell et al. |
| 2008/0287763 A1 | 11/2008 | Hayter |
| 2008/0288180 A1 | 11/2008 | Hayter et al. |
| 2008/0288204 A1 | 11/2008 | Hayter et al. |
| 2008/0312842 A1 | 12/2008 | Hayter et al. |
| 2008/0312844 A1 | 12/2008 | Hayter et al. |
| 2008/0312845 A1 | 12/2008 | Hayter et al. |
| 2009/0005665 A1 | 1/2009 | Hayter et al. |
| 2009/0006034 A1 | 1/2009 | Hayter et al. |
| 2009/0033482 A1 | 2/2009 | Hayter et al. |
| 2009/0036760 A1 | 2/2009 | Hayter |
| 2009/0054748 A1 | 2/2009 | Feldman |
| 2009/0108992 A1 | 4/2009 | Shafer |
| 2009/0294277 A1 | 12/2009 | Thomas et al. |
| 2010/0094110 A1 | 4/2010 | Heller et al. |
| 2010/0094111 A1 | 4/2010 | Heller et al. |
| 2010/0094112 A1 | 4/2010 | Heller et al. |
| 2010/0198034 A1 | 8/2010 | Thomas et al. |
| 2010/0198142 A1 | 8/2010 | Sloan et al. |
| 2010/0204557 A1 | 8/2010 | Kiaie et al. |
| 2010/0213057 A1 | 8/2010 | Feldman et al. |

(56) References Cited

U.S. PATENT DOCUMENTS

| | | |
|---|---|---|
| 2010/0230285 A1 | 9/2010 | Hoss et al. |
| 2010/0270150 A1 | 10/2010 | Wang et al. |
| 2010/0324392 A1 | 12/2010 | Yee et al. |
| 2010/0326842 A1 | 12/2010 | Mazza et al. |
| 2011/0021889 A1 | 1/2011 | Hoss et al. |
| 2011/0082484 A1 | 4/2011 | Saravia et al. |
| 2011/0106126 A1 | 5/2011 | Love et al. |
| 2011/0190603 A1 | 8/2011 | Stafford |
| 2011/0191044 A1 | 8/2011 | Stafford |
| 2011/0213225 A1* | 9/2011 | Bernstein ............ A61B 5/0017 600/309 |
| 2011/0256024 A1 | 10/2011 | Cole et al. |
| 2011/0257495 A1 | 10/2011 | Hoss et al. |
| 2011/0282175 A1 | 11/2011 | Geissler et al. |
| 2011/0288574 A1 | 11/2011 | Curry et al. |
| 2011/0319729 A1 | 12/2011 | Donnay et al. |
| 2012/0010642 A1 | 1/2012 | Lee et al. |
| 2012/0078071 A1 | 3/2012 | Bohm et al. |
| 2012/0190941 A1 | 7/2012 | Donnay et al. |
| 2012/0190942 A1 | 7/2012 | Donnay et al. |
| 2012/0190943 A1 | 7/2012 | Donnay et al. |
| 2012/0197098 A1 | 8/2012 | Donnay et al. |
| 2012/0197222 A1 | 8/2012 | Donnay et al. |
| 2013/0040573 A1 | 2/2013 | Hillyard et al. |
| 2013/0059541 A1 | 3/2013 | Sloan et al. |
| 2013/0150691 A1 | 6/2013 | Pace et al. |
| 2013/0150697 A1 | 6/2013 | Imai et al. |
| 2014/0031655 A1 | 1/2014 | Stafford |
| 2014/0275898 A1 | 9/2014 | Taub et al. |

FOREIGN PATENT DOCUMENTS

| | | |
|---|---|---|
| WO | WO 2012/160163 | 11/2012 |
| WO | WO 2005/112744 A1 | 12/2012 |
| WO | WO 2012/174538 | 12/2012 |
| WO | WO 2014/179343 A1 | 11/2014 |

OTHER PUBLICATIONS

Bluetooth Low Energy Technology Training, All Hands Meeting, Apr. 19-22, 2010.
Specification of the Bluetooth System, vol. 0—Master Table of Contents & Compliance Requirements, Covered Core Package version: 4.0, Jun. 30, 2010.
Specification of the Bluetooth System, vol. 1—Architecture & Terminology Overview, Covered Core Package version: 4.0, Jun. 30, 2010.
Specification of the Bluetooth System, vol. 2—Core System Package [BR/EDR Controller volume], Covered Core Package version: 4.0, Jun. 30, 2010.
Specification of the Bluetooth System, vol. 3—Core System Package [Host volume], Covered Core Package version: 4.0, Jun. 30, 2010.
Specification of the Bluetooth System, vol. 4—Host Controller Interface [Transport Layer], Covered Core Package version: 4.0, Jun. 30, 2010.
Specification of the Bluetooth System, vol. 5—Core System Package [AMP Controller volume], Covered Core Package version: 4.0, Jun. 30, 2010.
Specification of the Bluetooth System, vol. 6—Core System Package [Low Energy Controller volume], Covered Core Package version: 4.0, Jun. 30, 2010.
AU, 2014260023 First Examination Report, dated Jan. 31, 2018.
CN, 201480024659.9 Office Action, dated Jun. 1, 2017.
CN, 201480024659.9 Second Office Action, dated Jan. 4, 2018.
EP, 14792119.1 Supplementary Search Report, dated Dec. 6, 2016.
WO, PCT/US2014/035926 ISR and Written Opinion, dated Sep. 25, 2014.

\* cited by examiner

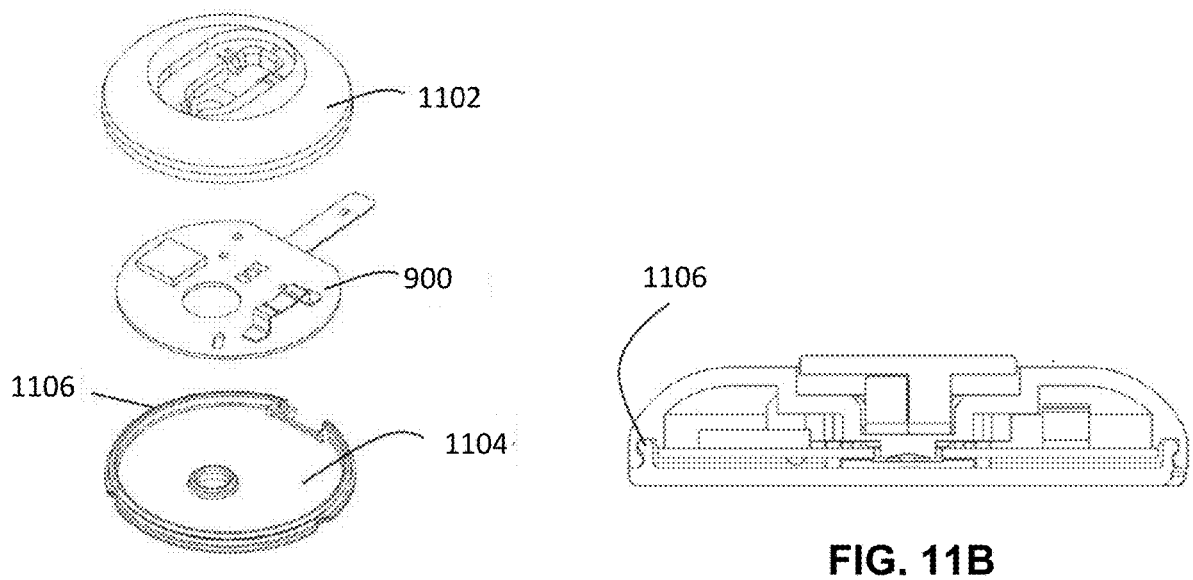
FIG. 11A
FIG. 11B
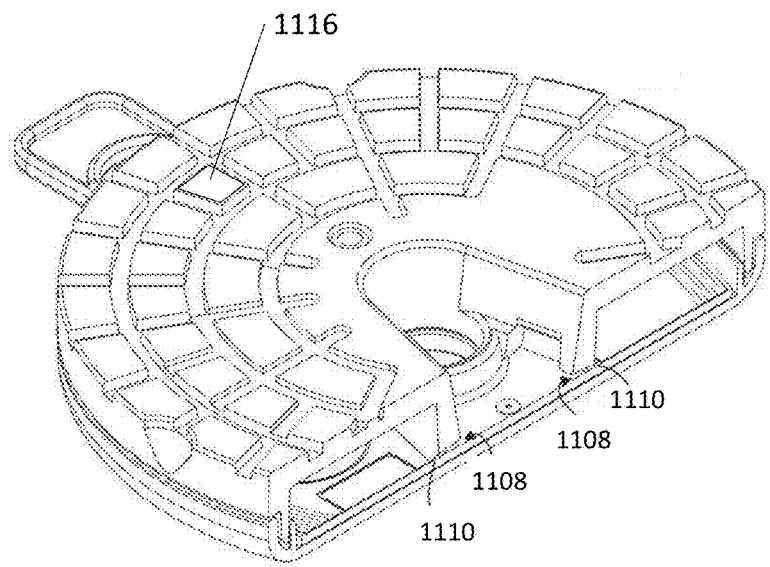
FIG. 11C

SYSTEMS, DEVICES, AND METHODS FOR ENERGY EFFICIENT ELECTRICAL DEVICE ACTIVATION

RELATED APPLICATIONS

The present application is a continuation of U.S. patent application Ser. No. 14/265,026, filed Apr. 29, 2014, which claims the benefit of and priority to U.S. Provisional Patent Application No. 61/973,775, filed Apr. 1, 2014, U.S. Provisional Patent Application No. 61/896,578, filed Oct. 28, 2013, and U.S. Provisional Patent Application No. 61/817,839, filed Apr. 30, 2013, all of which are incorporated by reference herein in their entireties for all purposes.

FIELD

The subject matter described herein relates generally to changing the state of power consumption of an electrical device in an efficient manner, for example, within an analyte monitoring environment.

BACKGROUND

The detection and/or monitoring of analyte levels, such as glucose, ketones, lactate, oxygen, hemoglobin A1C, or the like, can be vitally important to the health of an individual having diabetes. Diabetics generally monitor their glucose levels to ensure that they are being maintained within a clinically safe range, and may also use this information to determine if and/or when insulin is needed to reduce glucose levels in their bodies or when additional glucose is needed to raise the level of glucose in their bodies.

Growing clinical data demonstrates a strong correlation between the frequency of glucose monitoring and glycemic control. Despite such correlation, many individuals diagnosed with a diabetic condition do not monitor their glucose levels as frequently as they should due to a combination of factors including convenience, testing discretion, pain associated with glucose testing, and cost. For these and other reasons, needs exist for improved analyte monitoring systems, devices, and methods.

SUMMARY

A number of systems have been developed for the automatic monitoring of the analyte(s), like glucose, in a bodily fluid of a user, such as in the blood, interstitial fluid ("ISF"), dermal fluid, or in other biological fluid. Some of these systems include a sensor that can be at least partially positioned "in vivo" within the user, e.g., transcutaneously, subcutaneously, or dermally, to make contact with the user's bodily fluid and sense the analyte levels contained therein. These systems are thus referred to as in vivo analyte monitoring systems.

The sensor is generally part of a sensor control device that resides on (or in) the body of the user and contains the electronics and power source that enable and control the analyte sensing. The sensor control device, and variations thereof, can be referred to as a "sensor control unit," an "on-body electronics" device or unit, an "on-body" device or unit, or a "sensor data communication" device or unit, to name a few.

The analyte data sensed with the sensor control device can be communicated to a separate device that can process and/or display that sensed analyte data to the user in any number of forms. This device, and variations thereof, can be referred to as a "reader device" (or simply a "reader"), "handheld electronics" (or a handheld), a "portable data processing" device or unit, a "data receiver," a "receiver" device or unit (or simply a receiver), or a "remote" device or unit, to name a few. The reader device can be a dedicated use device, a smart phone, a tablet, a wearable electronic device such as a smart glass device, or others.

In vivo analyte monitoring systems can be broadly classified based on the manner in which data is communicated between the reader device and the sensor control device. One type of in vivo system is a "Continuous Analyte Monitoring" system (or "Continuous Glucose Monitoring" system), where data can be broadcast from the sensor control device to the reader device continuously without prompting, e.g., in an automatic fashion according to a broadcast schedule. Another type of in vivo system is a "Flash Analyte Monitoring" system (or "Flash Glucose Monitoring" system or simply "Flash" system), where data can be transferred from the sensor control device in response to a scan or request for data by the reader device, such as with a Near Field Communication (NFC) or Radio Frequency Identification (RFID) protocol.

Provided herein are a number of example embodiments of systems, devices, and methods that allow the state (or mode) of power consumption for a device, such as a sensor control device, to be changed in an energy efficient manner. Changing of the state of power consumption can include, for example, changing from a low power state (e.g., powered off) to a higher power state (e.g., powered on). In some cases, this change of state is referred to as "activation" and is employed, for example, when a sensor control device is first put in use by a wearer. For ease of illustration, many of the embodiments described herein will refer to changing the power state of a sensor control device, although these embodiments are not limited to such.

In certain embodiments an activation sensor is provided with the sensor control device and operation of the activation sensor causes activation of the internal electronics. The activation sensor can be an optical activation sensor that produces a response when exposed to ambient optical light or another light source. The exposure to light (or some other trigger such as a magnetic field) and subsequent activation can be accomplished before applying the device to the body of a user, for example, during the unpacking of the applicator assembly. The optical activation sensor can be part of an activation circuit for the sensor control device. Upon exposure to light, the optical activation sensor, which may be in the form of an optically activatable switch, can cause the activation circuit to initiate an on-board processor. The processor, in turn, can maintain the internal electronics in the active state during the duration of use of the sensor control device, or during the lifetime of the device's power supply. Verification of the initiation of the electronics can be performed by the user or automatically by the system, such as by generation of a message or other indication to the user at the reader device. Also provided are methods of manufacturing the sensor control device with a sensor control activation sensor such as an optical sensor.

In other embodiments, the sensor control device is capable of utilizing transmissions over a wireless communication protocol to change a power state, or to recognize when such a change should be effected.

For example, the sensor control device can be capable of sending and receiving communications according to a Bluetooth Low Energy (BTLE) protocol. In certain embodiments, the sensor control device, while operating in a first power state (e.g., a low power state such as a powered-off or inactivated state, a storage state, or a sleep state), can receive such a wireless communication from the reader device and recognize that it is or is part of a BTLE advertising sequence (or is a single advertising message). The recognition can be made either through hardware or software. Upon making that recognition, the sensor control device can change to a second, higher power state (e.g., a state of greater power consumption than the first power state, such as a powered-on or activated state, or an awake state). In certain embodiments, the sensor control device can recognize the advertising sequence without first demodulating the communication.

In some embodiments the sensor control device receives a second or subsequent advertising sequence from the reader device when in the second power state. The sensor control device can demodulate the second advertising sequence and determine if it contains an activation request message and, if so, then transmit a confirmation response to the reader device. If the demodulated communication does not contain the activation request message, then the state of the sensor control device can be changed back to the first power state. In some embodiments, the first power mode is a sleep (or storage) mode and the second power mode is a normal operation mode.

A number of variations to the aforementioned embodiments are also provided. For example, the advertising sequence can include a series of advertising packets transmitted at a predetermined time interval. The advertising sequence can include a connectable directed advertising packet type, a connectable undirected advertising packet type, a non-connectable undirected advertising packet type, or a scannable undirected advertising packet type, each of which can be the activation request message.

In still other embodiments, successive radio frequency (RF) communications can be used to supply power to, for example, the sensor control device. The sensor control device can be in a low-power state (e.g., a power-off or inactivated mode, a storage mode, or a sleep mode) where full operating power is not being supplied. The sensor control device can utilize the power of the received wireless communications to cause a local power source to begin supplying the operating power, thereby transitioning the sensor control device to a higher-power state (e.g., a normal, awake, or activated operating state). In many of these embodiments, the wireless communications are sent and received in accordance with a Near Field Communication (NFC) protocol, although other protocols can be used as well.

Adaptive embodiments are also described where the power mode of the sensor control device is directly or indirectly monitored by the reader device and one or more of the number, type, interval, or power of the successive wireless communications is adjusted by the reader device until sufficient power is supplied to enable the sensor control device to transition to a higher-power mode. The embodiments described herein are particularly suitable when the reader device is in the form of a smartphone.

Other systems, devices, methods, features and advantages of the subject matter described herein will be or will become apparent to one with skill in the art upon examination of the following figures and detailed description. It is intended that all such additional systems, devices, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIGS. 11A-C are assembly and sectional views of an alternative snap-together embodiment for the assembly of FIG. 9E.

DETAILED DESCRIPTION

The present subject matter is not limited to the particular embodiments described, as those are only examples and may, of course, vary. Likewise, the terminology used herein is for the purpose of describing particular embodiments only, and is not intended to be limiting, since the scope of the present disclosure will be limited only by the appended claims.

In conventional analyte monitoring systems, the sensor control device has a small physical form enabling it to be worn inconspicuously by the user. This constrains the size of the device's internal electronics and power source. If the sensor control device has a limited lifespan dictated by the long-term reliability of the sensor (e.g., fourteen days), then it will be disposable and replaceable with another device. The desirability to minimize the cost of each device adds further pressure to minimize the size of the power source and the rate at which it is used. The power requirements of the sensor control device electronics and the rate at which the software operates those electronics are therefore minimized in the design process.

To this end, the sensor control device is often shipped and stored in a low-power mode where the power source does not supply operating power to all or most of the sensor electronics. In some embodiments, only wireless communication circuitry is active, operating in a mode that draws minimal quiescent current to listen for an activation RF signal.

In this low-power mode the power source can be disconnected mechanically from the internal electronics (such as by placement of a removable insulator between the device's contacts and the power source), electronically (such as with a controllable isolation circuit) in a manner that minimizes leakage current from the source, or otherwise. The power source can be connected once the wearer is ready to begin use of the sensor.

Many of the embodiments described herein provide techniques for changing the power state of a sensor control device with improved efficiency, cost, and reduced hardware and software (among others) as compared to conventional techniques.

Figure 1:
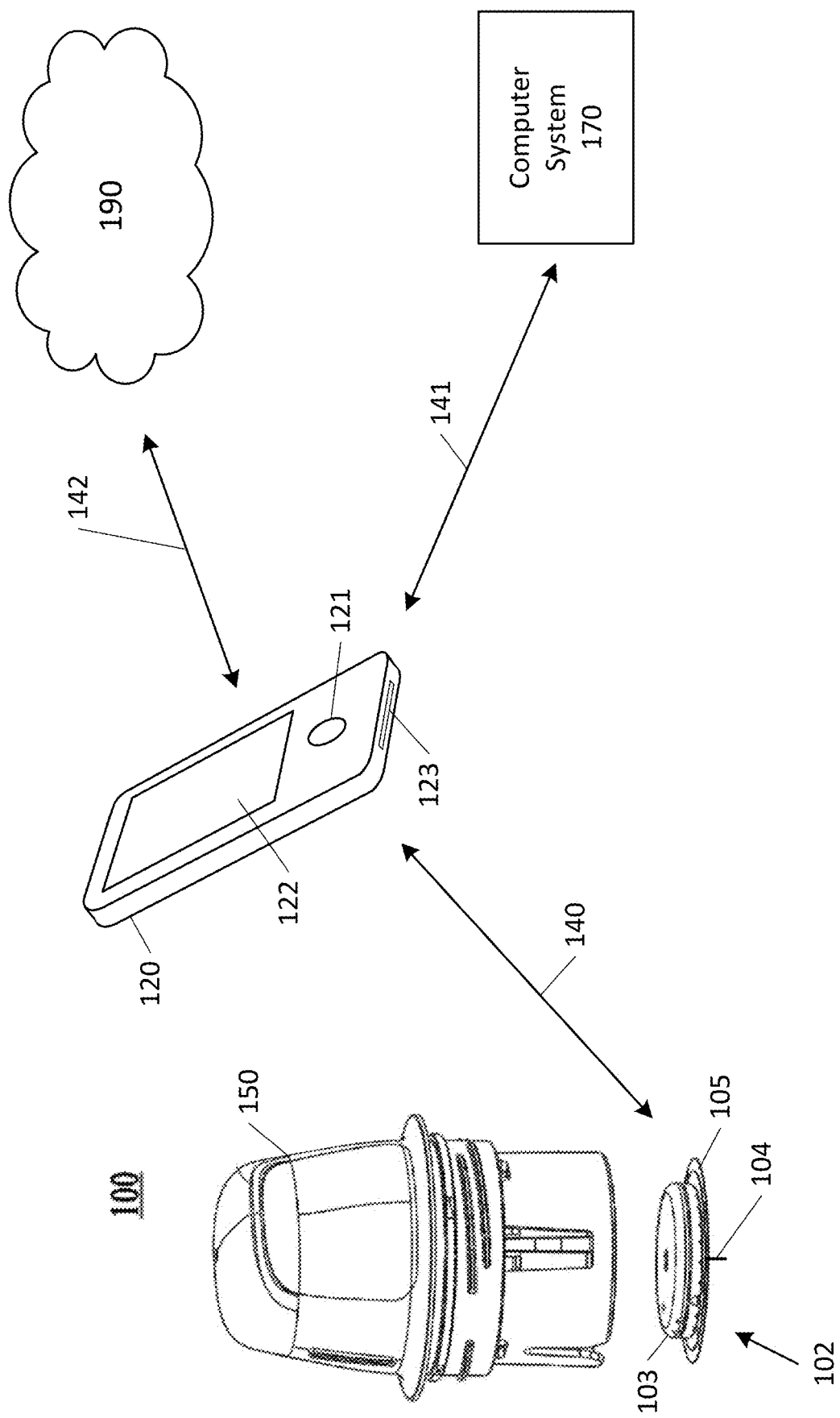
FIG. 1 is a high level diagram depicting an example embodiment of an analyte monitoring system for real time analyte (e.g., glucose) measurement, data acquisition and/or processing.

An example embodiment of an in vivo analyte monitoring system 100 with which the embodiments described herein can be used is depicted in the illustrative view of FIG. 1. Here, system 100 includes a sensor control device 102 and a reader device 120 that can communicate with each other over a local wireless communication path (or link) 140, which can be unidirectional or bi-directional. The communications sent across link 140 contain digital messages in a frame format (which includes packets) and can be based on a Near Field Communication (NFC) protocol (including an RFID protocol), Bluetooth or Bluetooth Low Energy (BTLE) protocol, Wi-Fi protocol, proprietary protocol, or others. Reader device 120 is also capable of wired, wireless, or combined communication over communication paths (or links) 141 and 142 with other systems or devices, such as a computer system 170 (e.g., a server for a website, a personal computer, a tablet, and the like) or cloud-based storage 190.

Any version of Bluetooth can be used for communication links 140, 141, and 142. One such version is Bluetooth Low Energy (BTLE, BLE), which is also referred to as Bluetooth SMART or Bluetooth SMART Ready. A version of BTLE is described in the Bluetooth Specification, version 4.0, published Jun. 30, 2010, which is explicitly incorporated by reference herein for all purposes. It should be noted that one of ordinary skill in the art will readily recognize that the embodiments described herein can be used with subsequent iterations of the Bluetooth protocols, or with new protocols that operate in a similar fashion to the Bluetooth protocols described herein, regardless of whether those protocols are in existence as of the time of this filing.

The use of BTLE communication (or other low-energy wireless standards), allows for reduced energy usage, which can be particularly important in performing data transmissions between sensor control device 102 and reader device 120 over link 140. This, in turn, allows for either reduction of the battery size in sensor control device 102 or extension of the battery life (or combinations thereof).

Use of a low-energy wireless communication protocol can allow the respective communication interfaces to have, for example, a lower duty cycle (i.e., less frequent active operation, which drains less battery power), shorter periods of usage, or any combination thereof. In addition to BTLE, other wireless protocols such as Wi-Fi, cellular, Zigbee, and custom protocols can be used instead of, or in addition to, BTLE for links 140, 141, and 142. These other protocols, however, typically require either more energy than BTLE, are not widely integrated into smartphones or tablets, or are not approved for worldwide use. Today and for the foreseeable future, smartphones, tablets, and other portable computing devices will be provided to customers with Bluetooth capability, as that family of protocols is widely regarded as the most convenient to accomplish close proximity communication between, e.g., a tablet, and the tablet's peripherals (e.g., wireless headset, mouse, keyboard, etc.).

Other embodiments of sensor control device 102 and reader device 120, as well as other components of an in vivo-based analyte monitoring system that are suitable for use with the system, device, and method embodiments set forth herein, are described in US Patent Application Publ. No. 2011/0213225 (the '225 Publication), which is incorporated by reference herein in its entirety for all purposes.

Figure 2A:
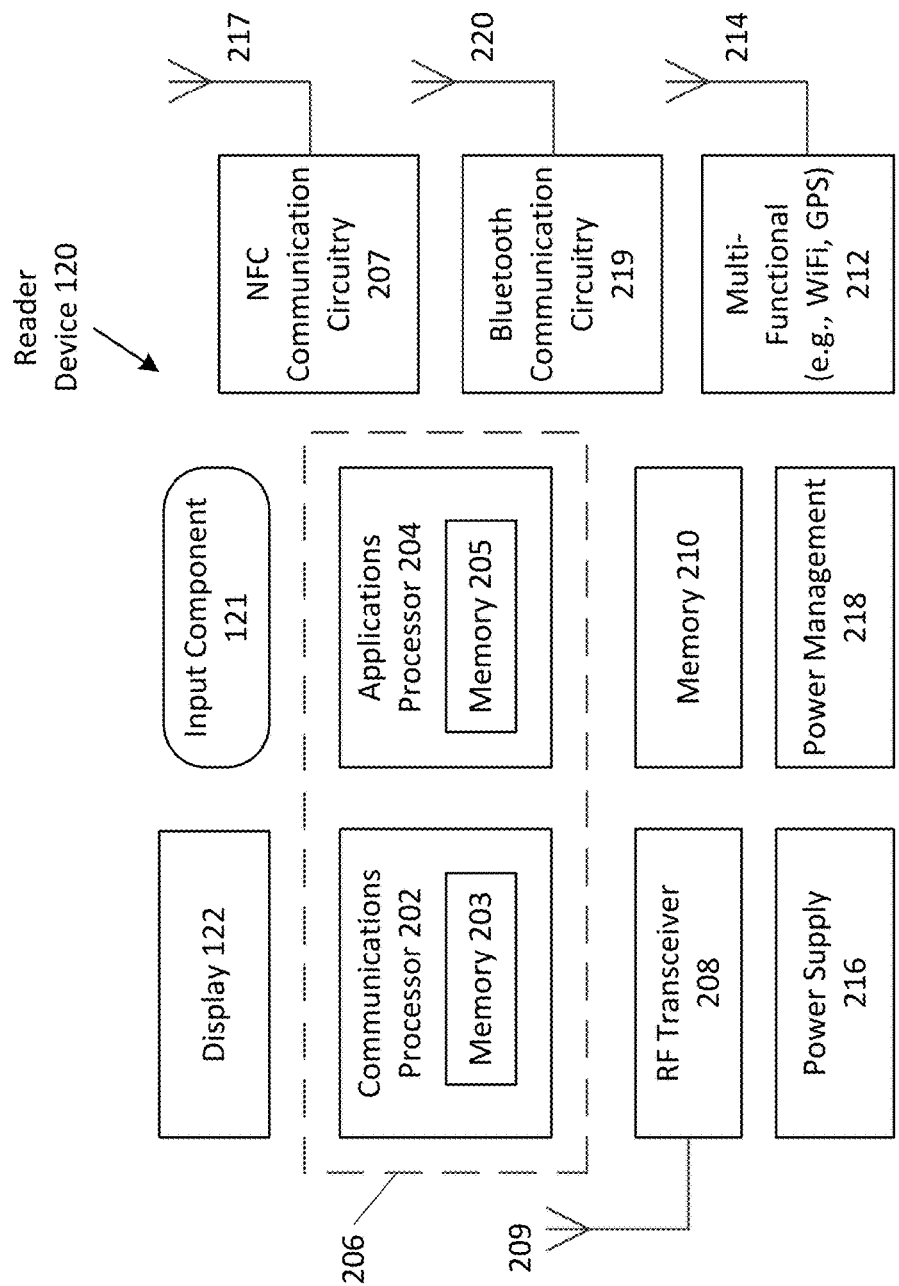
FIG. 2A is a block diagram depicting an example embodiment of a reader device configured as a smartphone.
Figure 2B:
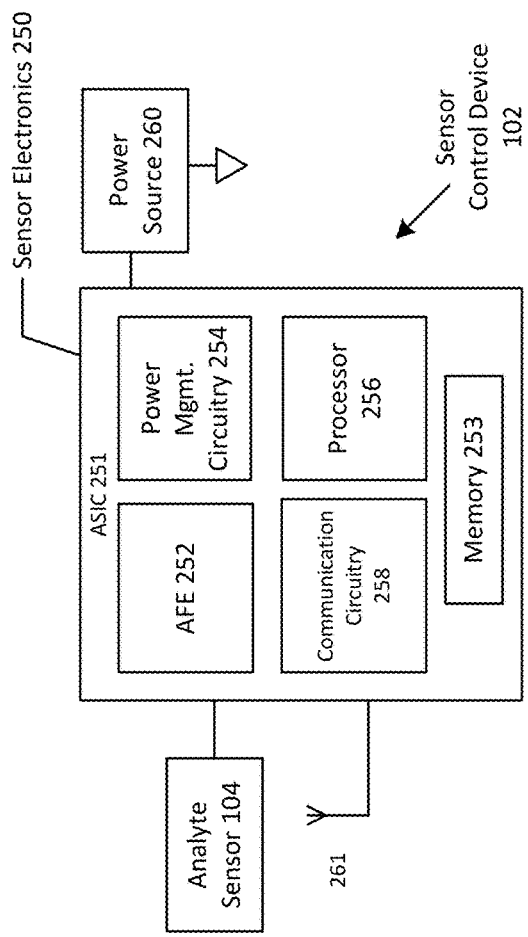
FIGS. 2B-C are block diagrams depicting example embodiments of a sensor control device.
Figure 2C:
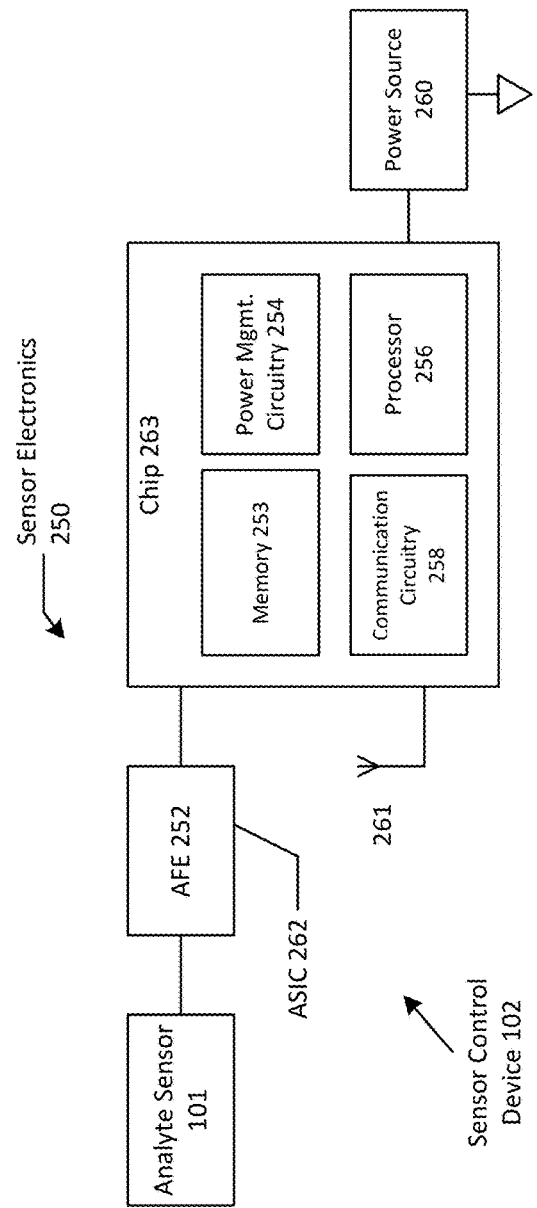

Sensor control device 102 can include a housing 103 containing in vivo analyte monitoring circuitry and a power source (shown in FIGS. 2B-C). The in vivo analyte monitoring circuitry is electrically coupled with an analyte sensor 104 that extends through a patch 105 and projects away from housing 103. An adhesive layer (not shown) can be positioned at the base of patch 105 for attachment to a skin surface of the user's body. Other forms of attachment to the body may be used, in addition to or instead of adhesive. Sensor 104 is adapted to be at least partially inserted into the body of the user, where it can make contact with the user's bodily fluid and, once activated, used with the in vivo analyte monitoring circuitry to measure and collect analyte-related data of the user. Generally, sensor control device 102 and its components can be applied to the body with a mechanical applicator 150 in one or more steps, as described in the incorporated '225 Publication, or in any other desired manner.

After activation, sensor control device 102 can wirelessly communicate the collected analyte data (such as, for example, data corresponding to monitored analyte level and/or monitored temperature data, and/or stored historical analyte related data) to reader device 120 where, in certain embodiments, it can be algorithmically processed into data representative of the analyte level of the user and then displayed to the user and/or otherwise incorporated into a diabetes monitoring regime.

As shown in FIG. 1, reader device 120 includes a display 122 to output information to the user and/or to accept an input from the user (e.g., if configured as a touch screen), and one optional user interface component 121 (or more), such as a button, actuator, touch sensitive switch, capacitive switch, pressure sensitive switch, jog wheel or the like. Reader device 120 can also include one or more data communication ports 123 for wired data communication with external devices such as computer system 170 (described below). Reader device 120 may also include an in vitro analyte meter, including an in vitro test strip port (not shown) to receive an in vitro analyte test strip for performing in vitro analyte measurements.

Computer system 170 can be used by the user or a medical professional to display and/or analyze the collected analyte data with an informatics software program. Computer system 170 may be a personal computer, a server terminal, a laptop computer, a tablet, or other suitable data processing device, and can be (or include) software for data management and analysis and communication with the components in analyte monitoring system 100.

The processing of data and the execution of software within system 100 can be performed by one or more processors of reader device 120, computer system 170, and/or sensor control device 102. For example, raw data measured by sensor 104 can be algorithmically processed into a value that represents the analyte level and that is readily suitable for display to the user, and this can occur in sensor control device 102, or it can occur in reader device 120 or computer system 170 after receipt of the raw data from sensor control device 102. This and any other information derived from the raw data can be displayed in any of the manners described above (with respect to display 122) on any display residing on any of sensor control device 102, reader device 120, or computer system 170. The information may be utilized by the user to determine any necessary corrective actions to ensure the analyte level remains within an acceptable and/or clinically safe range.

As discussed above, reader device 120 can be a mobile communication device such as, for example, a Wi-Fi or internet enabled smartphone, tablet, or personal digital assistant (PDA). Examples of smartphones can include, but are not limited to, those phones based on a WINDOWS operating system, ANDROID operating system, IPHONE operating system, PALM WEBOS, BLACKBERRY operating system, or SYMBIAN operating system, with data network connectivity functionality for data communication over an internet connection and/or a local area network (LAN).

Reader device 120 can also be configured as a mobile smart wearable electronics assembly, such as an optical assembly that is worn over or adjacent to the user's eye (e.g., a smart glass or smart glasses, such as GOOGLE GLASSES). This optical assembly can have a transparent display that displays information about the user's analyte level (as described herein) to the user while at the same time allowing the user to see through the display such that the user's overall vision is minimally obstructed. The optical assembly may be capable of wireless communications similar to a smartphone. Other examples of wearable electronics include devices that are worn around or in the proximity of the user's wrist (e.g., a watch, etc.), neck (e.g., a necklace, etc.), head (e.g., a headband, hat, etc.), chest, or the like.

FIG. 2A is a block diagram of an example embodiment of a reader device 120 in the form of a smartphone. Here, reader device 120 includes an input component 121, display 122, and processing hardware 206, which can include one or more processors, microprocessors, controllers, and/or microcontrollers, each of which can be a discrete chip or distributed amongst (and a portion of) a number of different chips. Processing hardware 206 includes a communications processor 202 having on-board memory 203 and an applications processor 204 having on-board memory 205. Reader device 120 further includes an RF transceiver 208 coupled with an RF antenna 209, a memory 210, NFC communication circuitry 207 coupled with antenna 217, Bluetooth communication circuitry 219 coupled with antenna 220, multi-functional circuitry 212 with one or more associated antennas 214, a power supply 216, and power management circuitry 218. FIG. 2A is an abbreviated representation of the internal components of a smartphone, and other hardware and functionality (e.g., codecs, drivers, glue logic, etc.) can, of course, be included.

Communications processor 202 can interface with RF transceiver 208 and perform analog-to-digital conversions, encoding and decoding, digital signal processing and other functions that facilitate the conversion of voice, video, and data signals into a format (e.g., in-phase and quadrature) suitable for provision to RF transceiver 208, which can then transmit the signals wirelessly. Communications processor 202 can also interface with RF transceiver 208 to perform the reverse functions necessary to receive a wireless transmission and convert it into digital data, voice, and video.

Applications processor 204 can be adapted to execute the operating system and any software applications that reside on reader device 120, process video and graphics, and perform those other functions not related to the processing of communications transmitted and received over RF antenna 209, such as the handling and formatting of NFC or Bluetooth communications. Any number of applications can be running on reader device 120 at any one time, and will typically include one or more applications that are related to a diabetes monitoring regime, in addition to the other commonly used applications, e.g., email, calendar, etc.

Memory 210 can be shared by one or more of the various functional units present within reader device 120, or can be distributed amongst two or more of them (e.g., as separate memories present within different chips). Memory 210 can also be a separate chip of its own. Memory 210 is non-transitory, and can be volatile (e.g., RAM, etc.) and/or non-volatile memory (e.g., ROM, flash memory, F-RAM, etc.).

NFC communication circuitry 207 can be implemented as one or more chips and/or components that perform controller functions (e.g., level and data mode detection, framing, etc.), analog-digital conversions (ADC and DAC), and analog interfacing with antenna 217 (e.g., the modulation and demodulation of NFC communications). Circuitry 207 can include a voltage-controlled oscillator (VCO), phase-locked loop (PLL) circuitry, a power amplifier for sending communications, and associated filters for waveform shaping. Antenna 217 can be implemented as a loop-inductor as is typical for NFC platforms.

Similarly, Bluetooth communication circuitry 219 can be implemented as one or more chips and/or components that perform controller functions (e.g., level and data mode detection, framing, etc.), analog-digital conversions (ADC and DAC), and analog interfacing with antenna 220 (e.g., modulation and demodulation). Bluetooth communication circuitry 219 can be configured to operate according to any of the Bluetooth standards described herein. Circuitry 219 can include a voltage-controlled oscillator (VCO), phase-locked loop (PLL) circuitry, a power amplifier for sending communications, and associated filters for waveform shaping.

Multi-functional circuitry 212 can also be implemented as one or more chips and/or components, including communication circuitry, that perform functions such as handling other local wireless communications (e.g., Wi-Fi) and determining the geographic position of reader device 120 (e.g., global positioning system (GPS) hardware). One or more other antennas 214 are associated with multi-functional circuitry 212 as needed. Reader device 120 can include all of NFC communication circuitry 207, Bluetooth communication circuitry 219, and multifunctional circuitry 212, or omit any one or more of those blocks (and associated antennas) as desired for the individual application, so long as a manner for communicating with sensor control device 102 is maintained.

Power source 216 can include one or more batteries, which can be rechargeable or single-use disposable batteries. Power management circuitry 218 can regulate battery charging and perform power source monitoring, boost power, perform DC conversions, and the like.

Structural and functional components similar to that described with respect to FIG. 2A can be present in reader device 120 in its other forms as well (e.g., as a dedicated use device, tablet, wearable device, and others). Additional examples of reader device 120 configured as a dedicated use device are described in the incorporated U.S. Provisional Application No. 61/817,839 and the '225 Publication.

FIG. 2B is a block diagram depicting an example embodiment of sensor control device 102 having analyte sensor 104 and sensor electronics 250 (including analyte monitoring circuitry). Although any number of chips can be used, here the majority of sensor electronics 250 are incorporated on a single semiconductor chip 251 that can be a custom application specific integrated circuit (ASIC). Shown within ASIC 251 are certain high-level functional units, including an analog front end (AFE) 252, power management (or control) circuitry 254, processor 256, and communication circuitry 258 for communications between device 102 and reader device 120. In this embodiment, both AFE 252 and processor 256 are used as analyte monitoring circuitry, but in other embodiments either circuit (or a portion thereof) can perform the analyte monitoring function. Processor 256 can include one or more processors, microprocessors, controllers, and/or microcontrollers.

A non-transitory memory 253 is also included within ASIC 251 and can be shared by the various functional units present within ASIC 251, or can be distributed amongst two or more of them. Memory 253 can be volatile and/or non-volatile memory. In this embodiment, ASIC 251 is coupled with power source 260, e.g., a coin cell battery. AFE 252 interfaces with in vivo analyte sensor 104 and receives measurement data therefrom, conditions the data signal, and outputs the data signal to processor 256 in analog form, which in turn uses an analog-to-digital converter (ADC) to convert the data to digital form (not shown) and then processes the data to arrive at the end-result analyte discrete and trend values, etc.

This data can then be provided to communication circuitry 258 for sending, by way of antenna 261, to reader device 120 (not shown) where further processing can be performed. Communication circuitry 258 can operate according to any of the NFC, Bluetooth, and Wi-Fi communication protocols described herein, or any other desired communication protocol, depending on the selected manner of communication with reader device 120. For example, communication circuitry 258 can include functional and discrete components similar to those of NFC communication circuitry 207 or Bluetooth communication circuitry 219 described with respect to FIG. 2A.

FIG. 2C is similar to FIG. 2B but instead includes two discrete semiconductor chips 262 and 263, which can be packaged together or separately. Here, AFE 252 is resident on ASIC 262. Processor 256 is integrated with power management circuitry 254 and communication circuitry 258 on chip 263. In one example embodiment, AFE 252 is combined with power management circuitry 254 and processor 256 on one chip, while communication circuitry 258 is on a separate chip. In another example embodiment, both AFE 252 and communication circuitry 258 are on one chip, and processor 256 and power management circuitry 254 are on another chip. Other chip combinations are possible, including three or more chips, each bearing responsibility for the separate functions described, or sharing one or more functions for fail-safe redundancy.

Incorporation of the majority, or all, of the data processing into sensor control device 102 allows reader device 120 to act mostly or entirely as a display and interface device for the user. This can provide an advantage in managing regulatory approval of system 100, as sensitive glucose calculations and related processing can be performed on the sensor control device 102 and not on an uncontrolled data processing device such as a commercially available smartphone. Conversion of a smartphone, or other similar commercially available device, into reader device 120 suitable for interfacing with sensor control device 102 can be accomplished by installing a software application (or "app") onto the smartphone in a conventional manner without any hardware additions or modifications. The software application need only interface with the appropriate communication circuitry (e.g., 207, 219, 212) on this smartphone to accept and display the end-result data from sensor control device 102 (glucose data, trend data, etc.).

The incorporation of algorithmic data processing within sensor control device 102, along with the use of a continuous wireless transmission protocol can also provide the advantage of allowing sensor control device 102 to readily interface with products provided by third parties or other manufacturers, such as other types of healthcare systems that do not have the on-board glucose data processing capabilities and/or algorithms. Examples of third party systems include continuous glucose monitoring systems, home health monitoring systems, hospital vital sign monitors, and closed loop systems (such as an artificial pancreas), or insulin pumps, and the like.

However, the data processing functions described herein can take place within the sensor control device 102 (as just described), reader device 120, computer system 170, or any combination thereof. This can include determinations of the user's analyte or glucose value, determinations of the variation or fluctuation of the monitored analyte level as a function of time, determinations of glucose trend over time, determinations of glucose rate of change, the occurrence of an alarm condition such as hypoglycemia or hyperglycemia or impending hypoglycemia or hyperglycemia, and any other data processing functions described herein (or with respect to data processing module 160 in the '225 Publication).

Example Embodiments for Changing the Power State Using External Stimuli Such as Optical or Magnetic Energy As described earlier, after the completion of the manufacturing process there may be an extended period of time during which system 100 is not used, for instance, while awaiting shipment, while being present "on the shelf," or while otherwise awaiting initial use by the customer or subject. During this time, sensor control device 102 may use minimal power in order to conserve the life of on-board power source 260. Sensor control device 102 may be in a low power state, or altogether deactivated if power source 260 is electrically isolated from the remainder of sensor electronics 250. Embodiments where the post-manufacturing initialization, or activation, is performed using wireless signals are described in the incorporated Provisional Application No. 61/817,839. The following embodiments can be freely substituted for those wireless-based embodiments.

Figure 3:
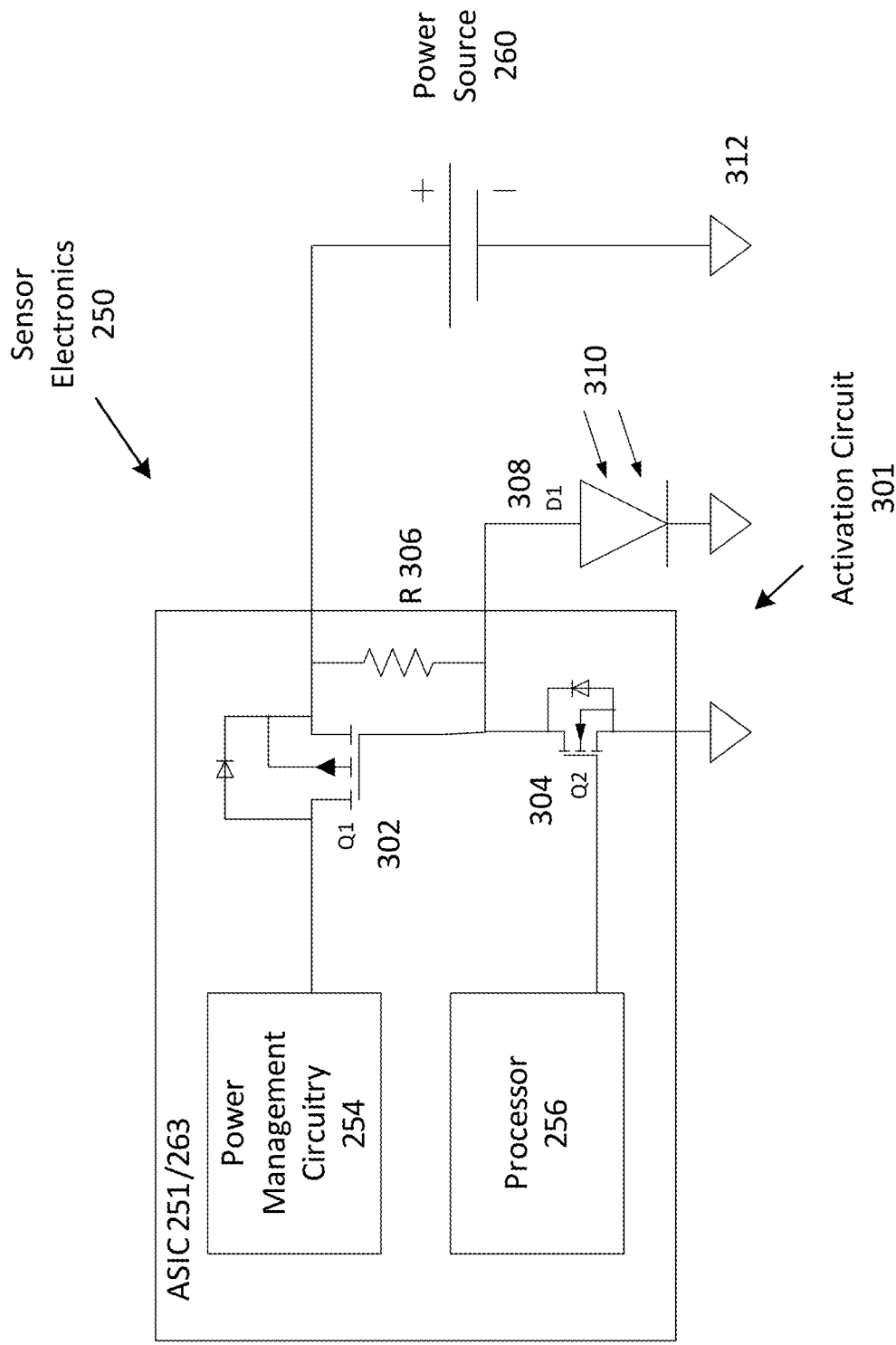
FIG. 3 is a block schematic view depicting an example embodiment of sensor electronics having an optically-based activation circuit.

FIG. 3 is a block schematic view depicting an example embodiment of sensor electronics 250 having an activation circuit 301. Here, activation circuit 301 is shown interposed between power source 260 and several functional components of sensor electronics 250. Specifically, those functional components are shown as power management circuitry 254 and processor 256, both of which are described with respect to FIGS. 2B-C as components of either a one chip embodiment (residing within ASIC 251) or a two chip embodiment (residing within chip 263), respectively. Therefore, the embodiment described with respect to FIG. 3 (and later FIG. 7) is applicable to devices having one chip, two chips, or more.

In this embodiment, activation circuit 301 includes a P-type MOSFET (PMOS) 302, an N-type MOSFET (NMOS) 304, a resistor 306, and an optical activation sensor 308 (also referred to herein as "optical sensor 308"), which, in this example, is an optically activatable switch 308. The positive terminal of power source 260 is coupled with a first terminal of resistor 306 and a source node of PMOS 302. The gate node of PMOS 302 is coupled with the opposite terminal of resistor 306, a drain node of NMOS 304, and a first terminal of optically activatable switch 308. The drain node of PMOS 302 is coupled with power management circuitry 254, and the gate node of NMOS 304 is coupled with processor 256. The negative terminal of power source 260, the opposite terminal of optically activatable switch 308, and the source node of NMOS 304 are each coupled with ground, or reference node, 312.

Optically activatable switch 308 is just one type of optical sensor. Optically activatable switch 308 can be any device that transitions from an open circuit (or current blocking state) to closed circuit (or current passing state) upon the incidence of radiation in the optical band (optical light). The larger field of optical sensors can include any device that produces a physical, thermal, or electrical response to the presence of optical light. Those of skill in the art will readily recognize that the response should be of sufficient magnitude to distinguish it from noise or other negligible responses. Other bands of radio frequency can be used to activate the switch, including ultraviolet, infrared, and so forth. Optically activatable switch 308 can be, for instance, a photodiode or phototransistor. Here, optically activatable switch 308 is shown as a photodiode that transitions from an open state (e.g., a low energy storage state in which current cannot flow) to a closed state (i.e., an active state in which current can flow) upon the receipt of sufficient optical radiation 310. In many embodiments, the amount of optical radiation 310 necessary to activate switch 308 is relatively low to ensure easy activation by the user at the appropriate time.

Upon receipt of a sufficient amount of radiation 310, photodiode 308 permits current to flow through resistor 306, which in turn causes the gate bias on PMOS pass transistor 302 to drop, thereby allowing current to flow from power source 260 to power management circuitry 254. Power management circuitry 254 is in communication with processor 256 and provides one or more commands or signals to processor 256 to initiate, or boot up, at which point processor 256 can perform an activation routine for sensor control device 102 that brings the remaining sensor electronics 250 into a higher power state.

This technique, as implemented in the optical, magnetic, and other embodiments herein, provides a significant advantage over conventional activation approaches. One such approach is that described in US Patent Publ. 2012/0078071 (Bohm et al.) where a processor must remain active, either by staying awake in a low-power mode or by being awoken in repeated fashion (e.g., each minute), in order to monitor for an interrupt signal (or other indicator) that the sensor device is ready to be taken out of a storage or other inactive mode. During these instances where the processor is in an active mode, even if the mode is a low power one, or only occurs for short intervals, the processor is functioning and drawing current from the power source at a greater rate, thereby depleting the stored charge of the power source and lessening the shelf life of the sensor device. This and other disadvantages are overcome with the embodiments described herein.

In certain embodiments, microprocessor 256 is capable of applying (and holding) a gate bias voltage to the gate of NMOS pass transistor 304 in order to allow current to flow across transistor 304 and thereby latch PMOS 302 in the "ON" state. Stated differently, processor 256 is capable of bypassing the optical sensor after changing the power state of device 102. Thus, should the light incident on the optical sensor (e.g., photodiode 308) become interrupted, sensor electronics 250 will remain active.

In many embodiments, optically activatable switch 308 operates with a relatively low dark current, for example, on the order of 10 nanoamps (nA) or less, so that switch 308 will not significantly impact the life of power source 260 during storage.

Although this embodiment has been described with respect to MOSFET devices, those of ordinary skill in the art will readily recognize that any number of other transistor types can be substituted for those described here, while achieving the same practical result. Also, in view of the disclosure contained herein and the schematic depicted in FIG. 3, those of ordinary skill in the art will readily recognize a number of other circuit designs that can take advantage of an optical sensor 308 to achieve the same or similar result. The existence of power management circuitry 254 as a separate functional component is optional as this function can be embedded within processor 256.

Still further, the components of activation circuit 301 can be implemented "on-chip" or "off-chip" or any combination thereof. (On-chip refers to the integration of the respective component with all other components on one semiconductor die.) Here, each of the components of activation circuit 301 is located on-chip with the exception of optically activatable switch 308, which is located off-chip. The placement of optically activatable switch 308 off-chip allows flexibility in the overall package design for sensor electronics 250, for example, by allowing optically activatable switch 308 to be placed in a location amenable to the receipt of sufficient light at the desired activation time.

Optical sensor 308 can be located within a housing of sensor control device 102, on the outer surface of sensor control device 102, or in a position coupled with the applicator (where it would later become detached upon deployment of sensor control device 102), so long as optical sensor 308 remains communicatively coupled with sensor electronics 250 so as to permit activation of those electronics.

Figure 4:
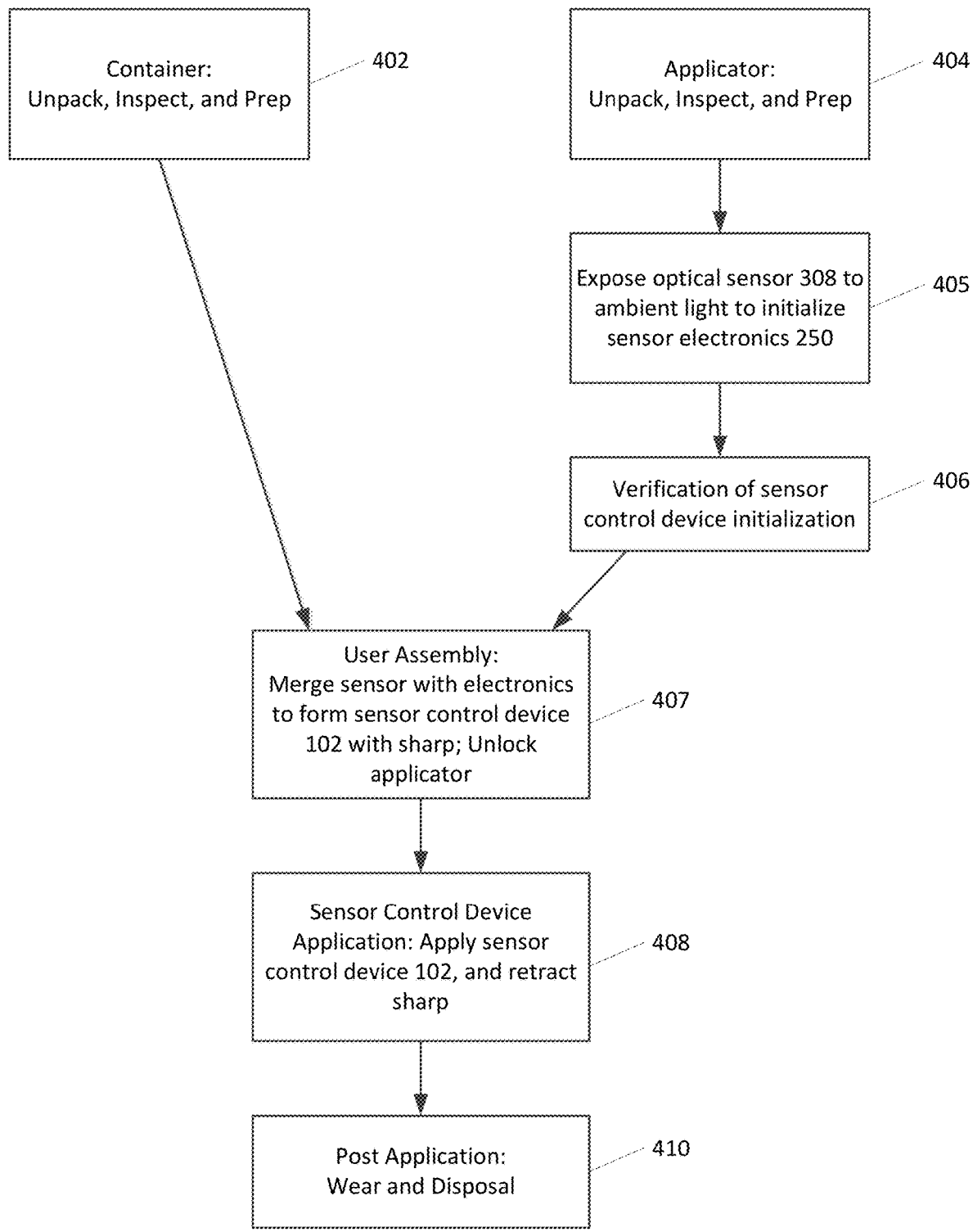
FIG. 4 is a flowchart depicting an example embodiment of a method of using the analyte monitoring system with an optical sensor.
Figure 5A:
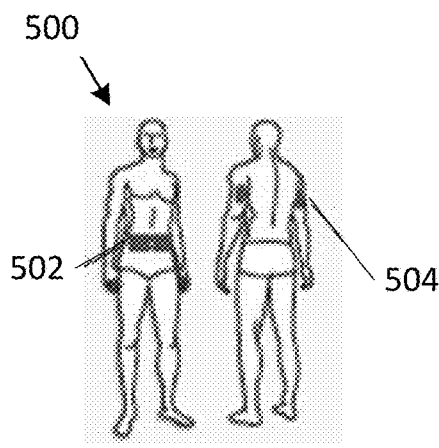
FIGS. 5A-I are illustrations of the steps in performing an example embodiment of a method of using the analyte monitoring system with an optical sensor.
Figure 5B:
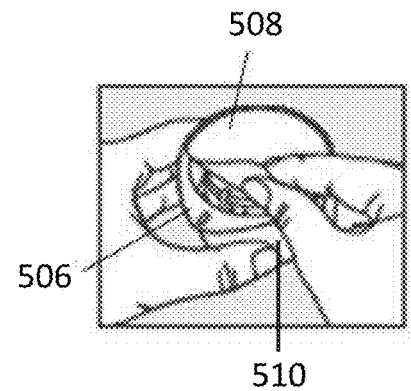

FIG. 4 is a flowchart depicting an example method 400 of using an optically activatable embodiment of system 100. FIG. 4 will be described in conjunction with the sequential diagrams of FIGS. 5A-G. A user 500 is depicted in FIG. 5A with example application sites 502 and 504. In some embodiments, other application sites may be used and a site preparation operation may optionally be performed. At 402 (FIG. 4), user 200 starts with unpacking a sensor container 506, such as is depicted in FIG. 5B. Container 506 can include a casing 510 which, in this embodiment, holds the sensor itself and an insertion sharp (or in some embodiments, the electronics assembly for controlling the sensor itself). Unpacking container 506 can include removing a container cover 508 that provides a sterile seal to the container contents.

Figure 5C:
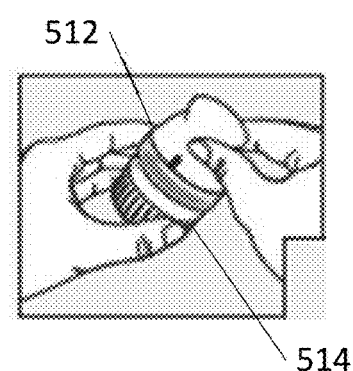
Figure 5D:
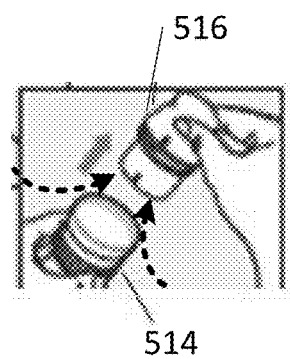

At 404 (FIG. 4), user 200 unpacks an applicator 512, which can include removing an applicator cover 514 (e.g., an end cap) that provides a sterile seal to the internal portion of an applicator assembly 516 as shown in FIGS. 5C-D. In this embodiment, the remainder of sensor control device 102, such as sensor electronics 250 and power source 216, as well as an overall housing for sensor control device 102, are present (obscured here) within application assembly 516. In embodiments where container 506 holds sensor electronics 250 in one assembly, then applicator assembly 516 can hold the sensor itself and the insertion sharp as another assembly. One reason for separating the two assemblies is to allow each to undergo separate sterilization processes.

In some embodiments, container 506 and applicator 512 can initially be packaged connected together to simplify packaging and shipping. Thus, in those embodiments, before removing cover 508 from the casing 510 and separating removable end cap 514 from applicator assembly 516, in an initial unpacking step, container 506 and applicator 512 are separated from each other.

At 405 (FIG. 4), user 500 exposes sensor control device 102 to ambient light, or a light bulb, LED, or other light source, in order to initiate optical sensor 308 (e.g., an optically activatable switch) contained within sensor control device 102. At this point, sensor electronics 250 become activated and sensor control device 102 can begin communication with reader device 120. Step 405 can be a positive step, such as the user physically directing the light-sensitive optical sensor 308 towards the light source. Step 405 can also be a direct result of removal of the applicator cover in step 404, in which case ambient light can immediately propagate into applicator assembly 516 as depicted by the dashed arrows of FIG. 5D, and impinge upon optical sensor 308, in a configuration such as that described with respect to FIG. 12C. In another embodiment, optical sensor 308 can be covered by a door, patch, sticker, or other opaque structure, and exposure to the requisite amount of light occurs by removal of that door, patch, sticker, or other opaque structure.

At 406 (FIG. 4), the initialization, or activation, of sensor electronics 250 is verified. This can be performed automatically by sensor control device 102 or reader device 120. For instance, in one embodiment a successful initialization of sensor electronics 250 will enable communications to be transmitted from sensor control device 102 to reader device 120, at which point reader device 120 can generate an indication or message to the user that sensor electronics 250 were successfully activated. In another embodiment a visual, auditory, vibrational, or tactile output is generated by sensor control device 102 that indicates successful activation to the user.

Figure 5E:
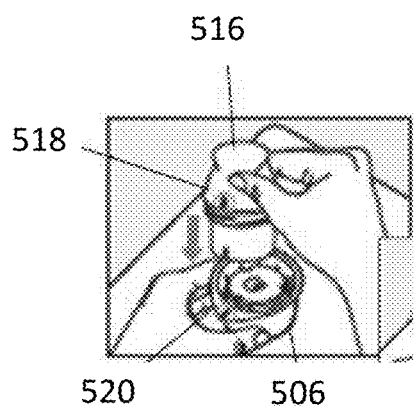
Figure 5F:
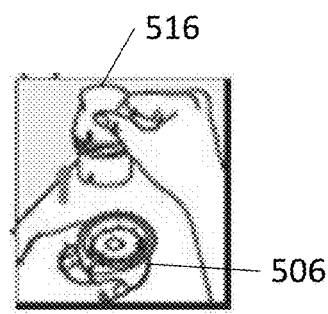

Next, in an assembly operation 407 (FIG. 4), applicator 512 is inserted into container 506 to merge or connect the sensor assembly and the sensor electronics assembly together to form sensor control device 102 and an insertion needle or sharp. As shown in FIG. 5E, once corresponding alignment indicators 518 and 520 are aligned, a first part of the user assembly operation 407 is carried out by pushing applicator assembly 516 firmly into container 506 to retrieve a sensor and a sharp from container 506 and to unlock a guide sleeve of applicator assembly 516. Applicator assembly 516 is then removed with the sensor and sharp from container 506, as shown in FIG. 5F.

Figure 5G:
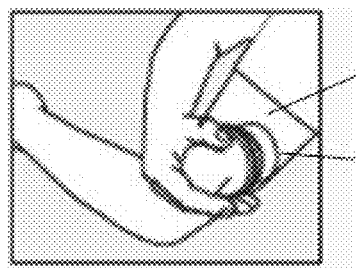
Figure 5H:
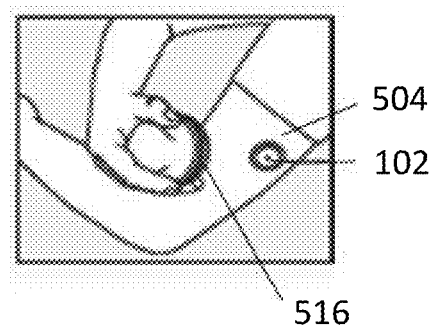

Next, once the user has chosen an application site, a sensor control device application operation 408 (FIG. 4) is performed. User 500 places applicator assembly 516 on the skin of the insertion site 504 and then applies an uncontrolled force to install sensor control device 102, as shown in FIG. 5G. Applicator 516 is manually pushed to insert the distal end of the sensor itself through the user's skin and to adhere sensor control device 102 to the skin surface. The sharp can be automatically retracted into applicator assembly 516 for disposal, at which point applicator assembly 516 can be manually removed from site 504, as shown in FIG. 5H.

In some embodiments, user 500 performs application operation 408 by applying an uncontrolled force to applicator assembly 516 where the uncontrolled force is applied in a single, continuous pushing motion along the longitudinal axis of applicator assembly 516 that once started, causes applicator assembly 516 to perform the application operation 408 such that applicator assembly 516 does not stop operation until completion. Applicator assembly 516 can be configured to relay action/audible cues to user so 500 that all three of the above listed actions happen automatically in response to applying the force to the applicator causing it to trigger.

Figure 5I:
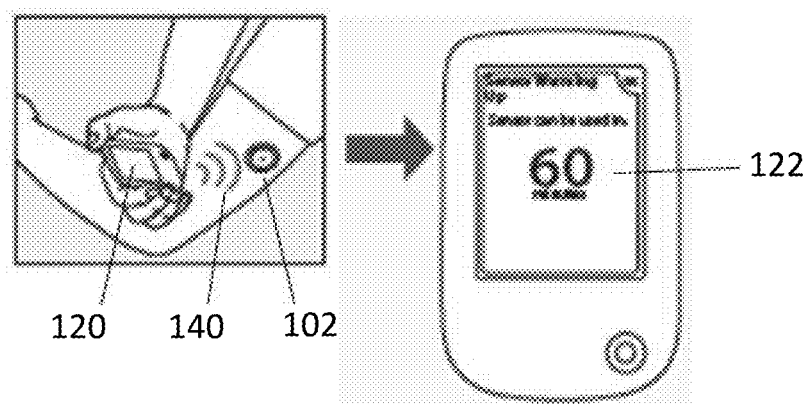

Advantageously, an adhesive of sensor control device 102 does not contact the user until the downward travel of applicator assembly 516 has completed. So, even after applicator assembly 516 has been placed on the skin, it can be moved to a different location as many times as desired until application operation 408 is actually carried out, and this is without damage to the apparatus or other system components. In a post-application stage 410, use of sensor control device 102 for monitoring the user's analyte level occurs during wear followed by appropriate disposal. An example of such a stage is depicted in FIG. 5I, where analyte levels detected by the sensor of sensor control device 102 can be retrieved over a wireless communication link 140 via a reader device 120. Relevant information (e.g., analyte level trend data, graphs, etc.) is presented on the reader device's display 122.

Steps 405 (light exposure) and 406 (initialization) were described above as being performed prior to step 407, however, in some embodiments steps 405 and 406 are performed after step 407, and in other embodiments steps 405 and 406 are performed after step 408. Also, step 406 can be performed immediately after step 405 or with one or more intervening steps.

Additional details regarding the method steps described with respect to FIGS. 4 and 5A-I can be found in the incorporated U.S. Provisional Application No. 61/817,839.

Figure 6A:
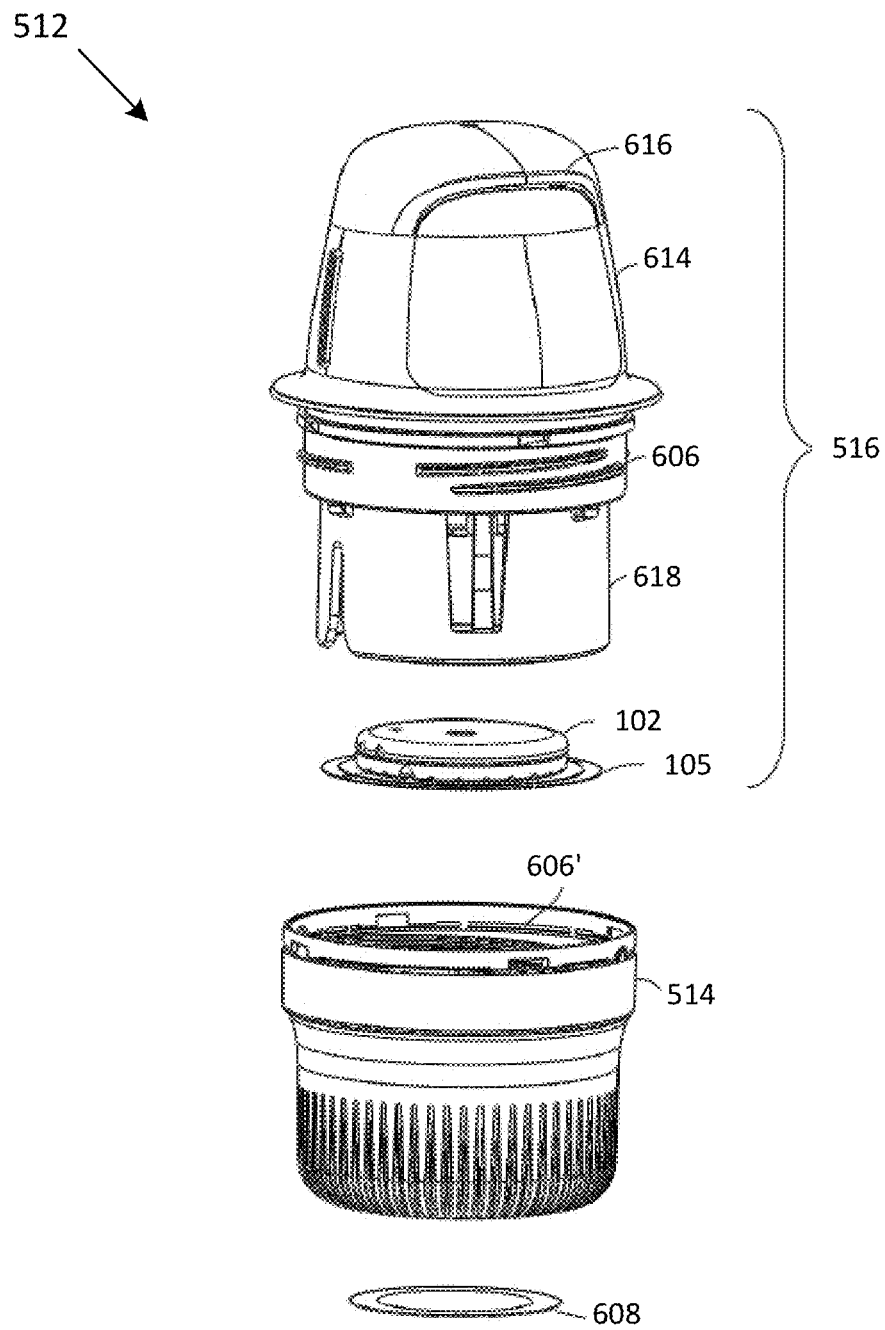
FIG. 6A is an exploded view of an example embodiment of an applicator.
Figure 6B:
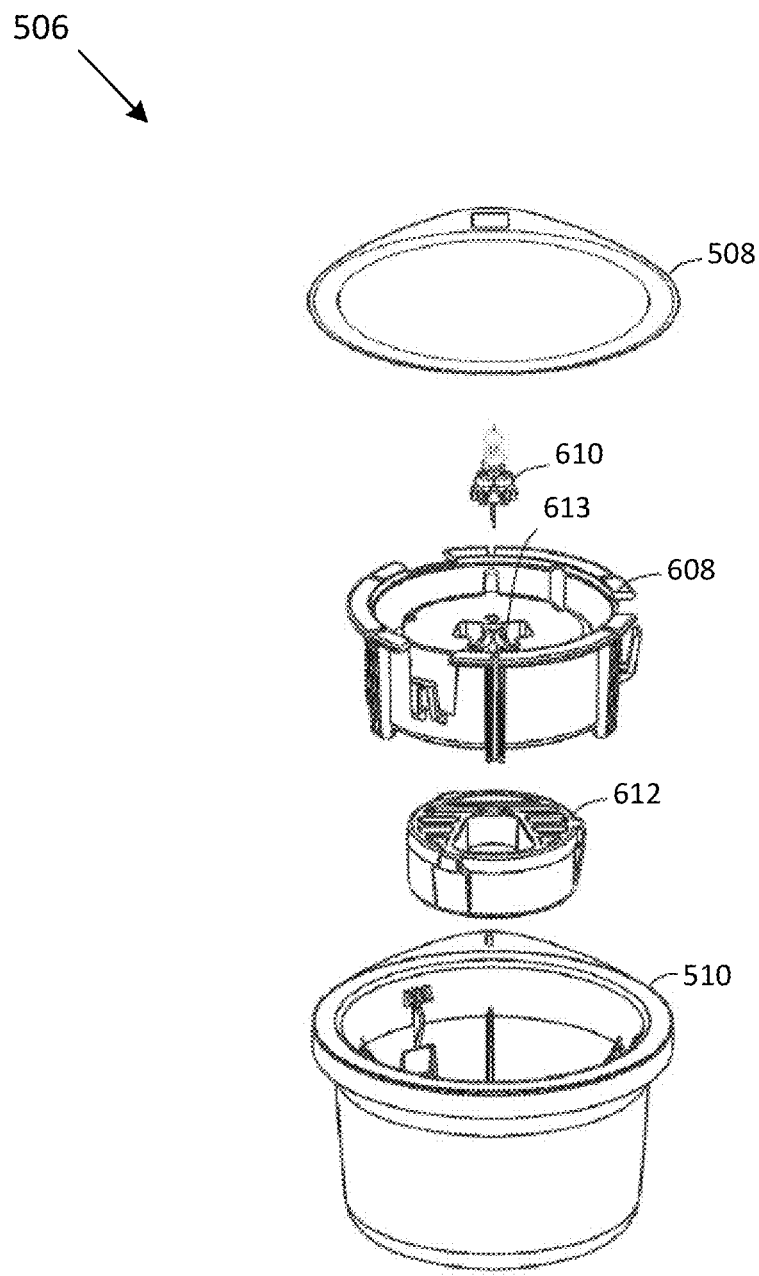
FIG. 6B is an exploded view of an example embodiment of a container for a sensor assembly.

Applicator 512, container 506, and the associated components shown in FIGS. 5A-I are illustrated in more detail in FIGS. 6A and 6B. In addition, numerous other variations are described in detail below. These alternative embodiments may operate differently insofar as their internal workings, but may present no difference concerning user activity.

Turning to FIG. 6A, applicator 512 includes a removable cap 514 (a type of cover) and applicator assembly 516. Removable cap 514 can be secured to applicator assembly 516 via complementary threads 606 and 606'. End Cap 514 fits with applicator assembly 516 to create a sterile packaging for the applicator interior. Therefore, no additional packaging is required to maintain sterility of the interior of applicator assembly 516.

In some embodiments, the end (not visible) of removable end cap 514 can include one or more openings, which can be sealed by a sterile barrier material such as DuPont™ Tyvek®, or other suitable material, to form seal 608. Such provision allows for ethylene oxide (ETO) sterilization of the applicator 512 through seal 608 when closed. In some embodiments, the openings in removable cap 514 may not be present and removable cap 514 may be made from a sterile process-permeable material so that the interior of applicator assembly 516 can be sterilized when cap 514 is mated to it, but that maintains sterility of the interior of the cap after exposure to the sterility process. In some embodiments, ETO sterilization is compatible with the electronics within sensor electronics 250 and with the associated adhesive patch 105, both of which can be releasably retained within applicator assembly 516 until applied to the user. As shown, applicator assembly 516 includes a housing 614 including integrally formed grip features 616 and a translating sheath or guide sleeve 618.

In reference to FIG. 6B, container 506 includes a cover 508 (e.g., made of a removable material such as foil) and casing 510. Housed within casing 510 is a desiccant body 612 and a table or platform 608. A sensor assembly 610 is snap-fit or otherwise held by the sensor assembly support 613. Sensor assembly 610 can also be snap-fit or otherwise held by the platform 608 (e.g., using fingers). With cover 508 sealed, container 510 can be subjected to gamma or radiation (e.g., e-beam) sterilization, an approach compatible with the chemistry of the sensor included in sensor assembly 610. Like applicator 512, container 506 is its own sterile packaging so that no additional packaging, other than casing 510 and cover 508, is required to maintain sterility of the interior of the casing.

Figure 7:
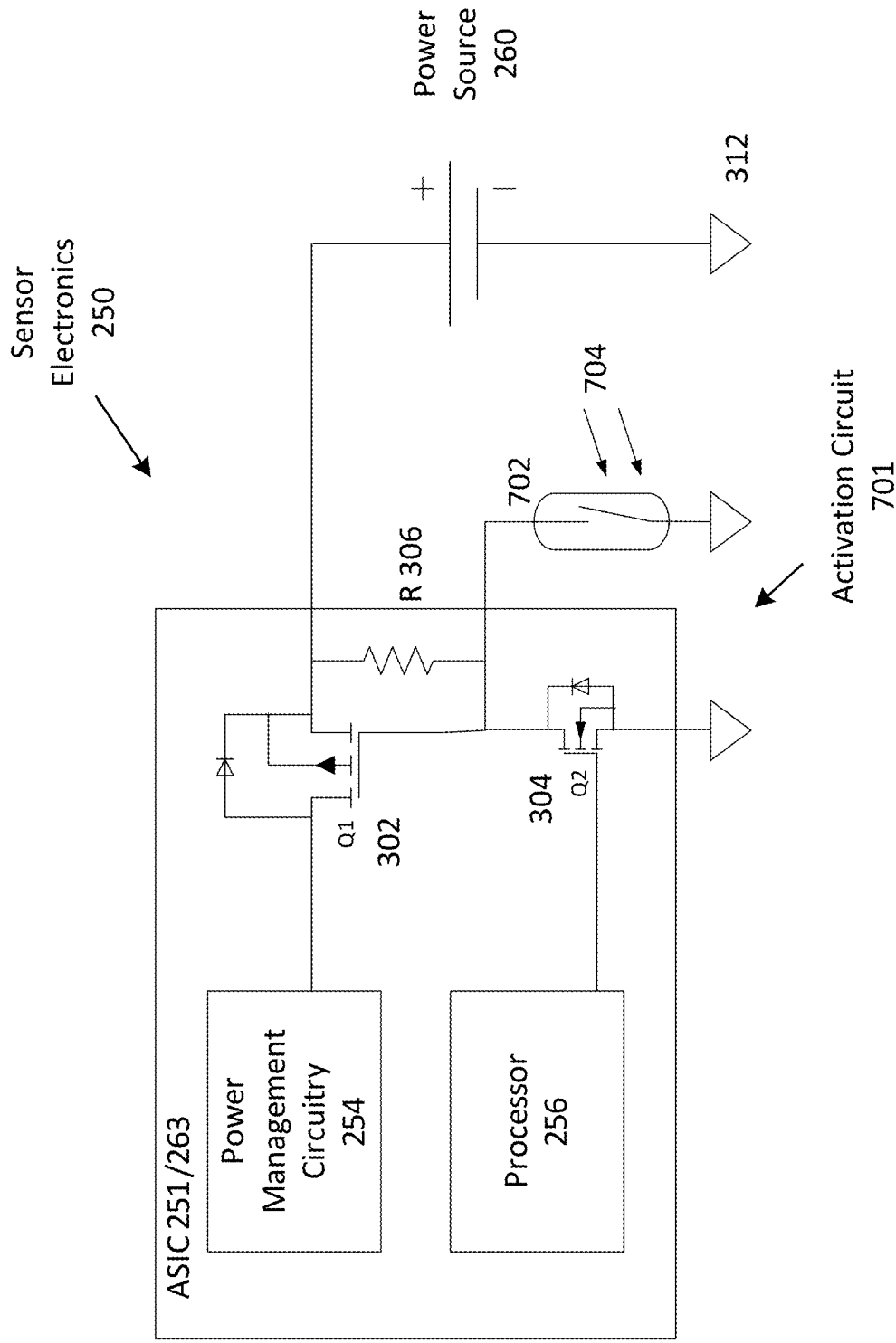
FIG. 7 is a block schematic view depicting an example embodiment of sensor electronics having a magnetically-based activation circuit.

In addition to optical manners of activation, other types of activation can be used with sensor control device 102. One such example is magnetic activation. FIG. 7 is a block schematic diagram depicting an example embodiment of sensor electronics 250 configured to be magnetically activatable. Here, activation circuit 701 is essentially the same as that depicted in FIG. 3 (and has the same advantages as those described with respect to FIG. 3) except that optically activatable switch 308 is replaced with a magnetic activation sensor 702 (also referred to herein as "magnetic sensor 702"), which in this embodiment is a magnetically activatable switch. Magnetic sensor 702 can be any device that produces a measurable output in response to the presence of a magnetic field 704. Magnetically activatable switch 702 can be any switch that will transition from a closed to open state upon the application of a sufficient magnetic field 704, or any device that will generate current flow to bias a pass transistor in activation circuit 701 upon application of a sufficient magnetic field 704. FIG. 7 shows magnetically activatable switch 702 as a Reed switch, but other static devices can be used such as a Hall effect sensor, and the like, or other dynamic devices.

The operation of the embodiment in FIG. 7 is essentially the same as described with respect to FIG. 3 except that instead of the application of sufficient light, the application of a sufficient magnetic field 704 causes magnetically activatable switch 702 to transition from an open state to a closed state that permits current to flow through resistor 306. Magnetic field 704 can be applied by bringing a permanent or time-varying magnet into proximity with magnetically activatable switch 702. For instance, system 100 can be provided to the user with a permanent magnet that is stored in the packaging of activator assembly 516 at a distance sufficient to prevent activation until the user physically brings the magnet into close proximity with switch 702. Alternatively, the magnet can be provided in separate packaging, and so forth.

Magnetic sensor 702 can be located within a housing of sensor control device 102, on the outer surface of sensor control device 102, or in a position coupled with applicator 512, so long as magnetic sensor 702 remains communicatively coupled with sensor electronics 250 so as to permit activation of those electronics 250.

Figure 8:
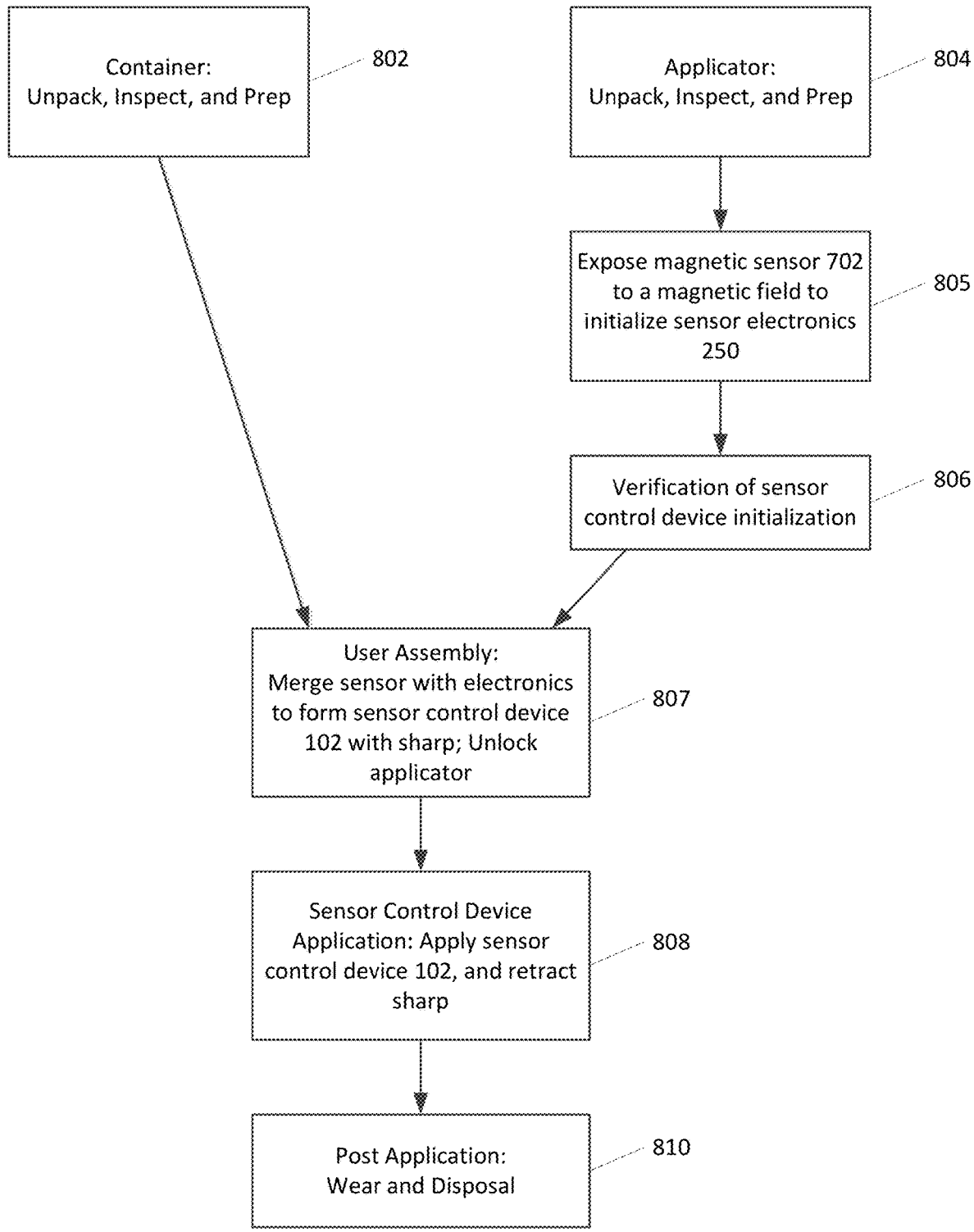
FIG. 8 is a flowchart depicting an example embodiment of a method of using the analyte monitoring system with a magnetic sensor.

FIG. 8 is a flowchart depicting an example method 800 of using a magnetically activatable embodiment of system 100. Many of the steps described here are the same as those described with respect to FIG. 4, so some common details will not be repeated. A user starts with unpacking container 506 at 802 and unpacking applicator 512 at 804. Unpacking container 506 at 802 can include removing cover 510 that provides a sterile seal to the container contents. Unpacking applicator 512 at 804 can include removing end cap 514 that provides a sterile seal to the internal portion of applicator assembly 516.

At 805, the user exposes sensor control device 102 to a magnetic field, for example, by bringing sensor control device 102 and/or a magnet into close proximity with each other, in order to initiate magnetic sensor 702 contained within sensor control device 102. At this point, sensor electronics 110 become activated and sensor control device 102 can begin communication with reader device 120. It should be noted that step 805 can be a positive step, such as the user physically bringing the magnetically-sensitive region of applicator 512 towards the source of the magnetic field (or vice versa), or step 805 can be a direct result of removal of applicator cover 514, such as by removal of a magnetic field supplied by a magnet in or on cover 514, which in turn causes activation of electronics 250.

At 806, the initialization, or activation, of sensor electronics 250 is verified. This can be performed automatically by communication between sensor control device 102 and reader device 120. For instance, in one embodiment a successful initialization of sensor electronics 250 will enable a communication to be transmitted from sensor control device 102 to reader device 120, at which point reader device 120 can generate an indication or message to the user that sensor electronics 250 were successfully activated. In another embodiment a visual, auditory, vibrational, or tactile output is generated by sensor control device 102 that indicates successful activation to the user.

The method of use can proceed with steps 807, 808, and 810 in the same manner as described with respect to FIG. 4. Steps 805 (exposure) and 806 (initialization) were described above as being performed prior to step 807, however, in some embodiments steps 805 and 806 are performed after step 807, and in other embodiments steps 805 and 806 are performed after step 808. Also, step 806 can be performed immediately after step 805 or with one or more intervening steps.

Other examples of manners of initialization include the use of near field communication (NFC), cellular energy, Bluetooth energy, Wi-Fi energy, and the like. These types of RF energy can be applied by dedicated devices sold with system 100, or by commercially available devices that can be integrated by the user into system 100, for example, a smartphone or tablet.

In one embodiment, placement of sensor control device 102 into proximity with the user's skin or body will be sensed by a temperature sensitive device that can be used to activate sensor electronics 250. The temperature sensitive device can be a differential device that can distinguish the body temperature of the user from what could be a relatively high ambient temperature. Upon detection of a sufficient gradient between the ambient temperature and the temperature of the user's body (expected to be a typical human body temperature), the temperature sensitive device will become enabled and activate operation of electronics 250, such as by closing a circuit to the power source.

Alternatively, a mechanical switch can be present on device 102, the actuation of which initiates electronics 250 therein. In yet another alternative embodiment, a shorting bar or shorting path can be used. For example, sensor assembly 610 (FIG. 6B) can have a conductive path either entirely exposed or with at least two exposed surfaces. Sensor control device 102 can have exposed leads, where the gap between the leads is an open circuit that prevents the supply of power from the power source or battery to the remainder of electronics 250. When sensor assembly 610 is brought into contact with the remaining portion of sensor control device 102, the exposed leads on device 102 come into contact with exposed portions of the conductive path on or in sensor assembly 610. The exposed leads on device 102 are then shorted together by the conductive path of sensor assembly 610, thereby activating electronics 250.

The construction of an example embodiment of sensor control device 102 described with respect to the following FIGS. 9A-12C is similar to that described in U.S. patent application Ser. No. 13/710,460, filed Dec. 11, 2012, and U.S. Provisional Application No. 61/569,287, filed Dec. 11, 2011, both of which are incorporated by reference herein for all purposes. In the present description, sensor control device 102 is described with features that facilitate optical activation.

Figure 9A:
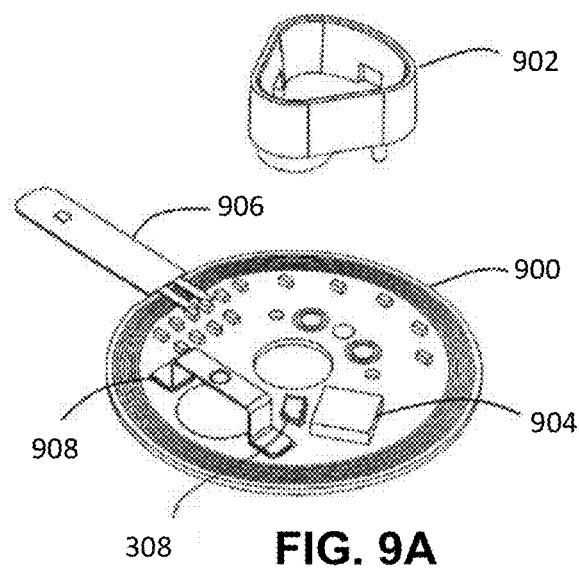
FIGS. 9A-D are construction views of a sensor control device subassembly.
Figure 9B:
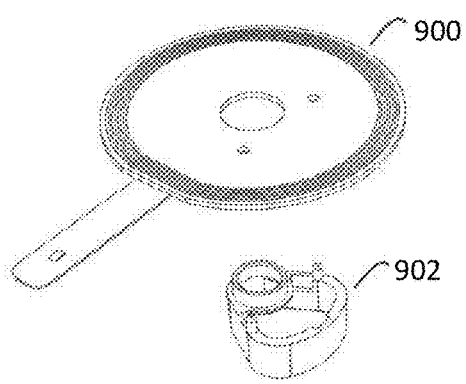
Figure 9C:
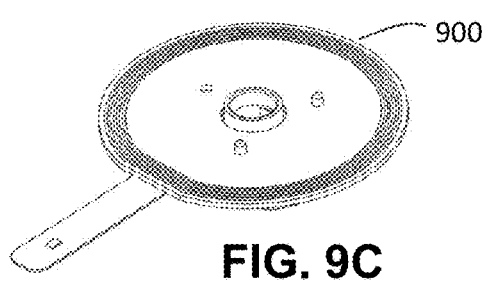
Figure 9D:
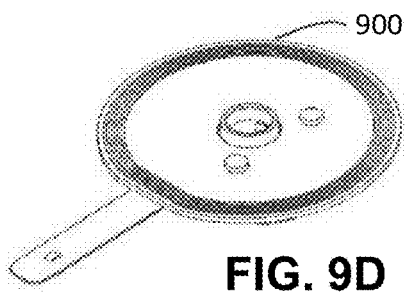
Figure 9E:
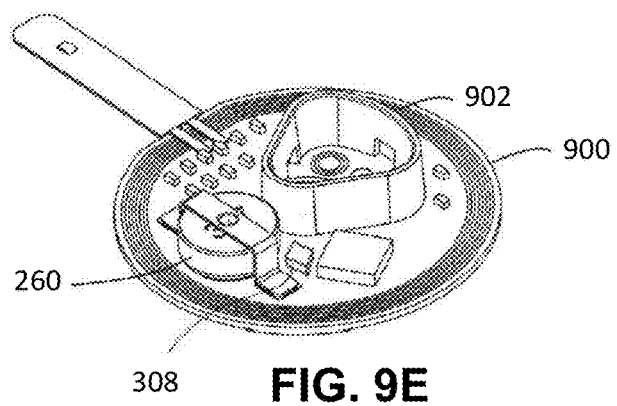
FIG. 9E is a perspective view of a complete sensor electronics subassembly.

FIGS. 9A-D provide top (FIG. 9A) and bottom (FIGS. 9B-D) construction views of an example sensor control device subassembly. A socket 902 or mount is fit through vias in a printed circuit board 900 along with other associated components including a processor 904 (e.g., an ASIC including a communications facility), thermistor/thermocouple 906, a battery mount 908, optical sensor 308, etc. Once circuit board 900 has been populated with these components, socket 902 is adhered to circuit board 900 (e.g., using heat stakes) as shown in FIGS. 9C-D. Once battery 260 is set in place, circuit board 900 as shown in FIG. 9E is prepared for incorporation into sensor control device 102.

Figure 10A:
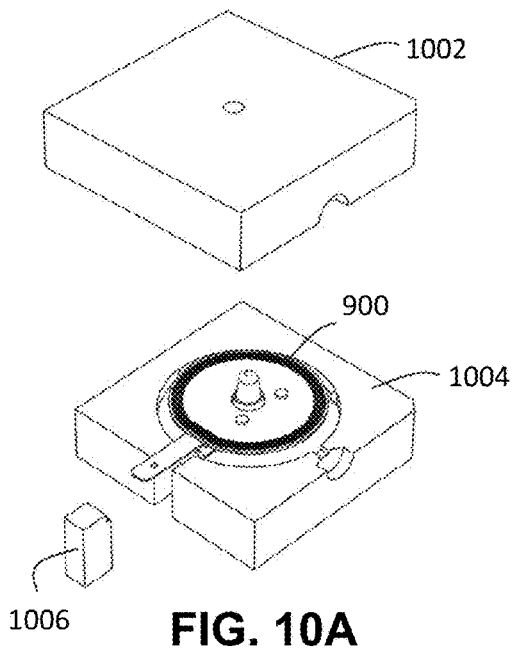
FIGS. 10A-D illustrate the process of co-molding/over-molding the embodiment of FIG. 9E.
Figure 10B:
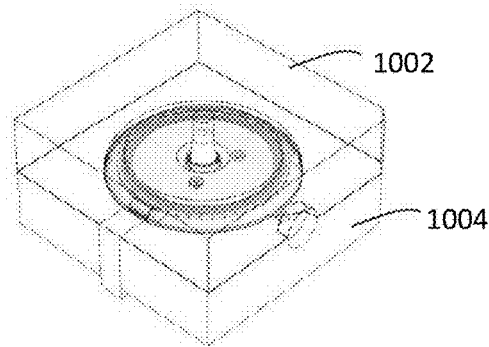
Figure 10C:
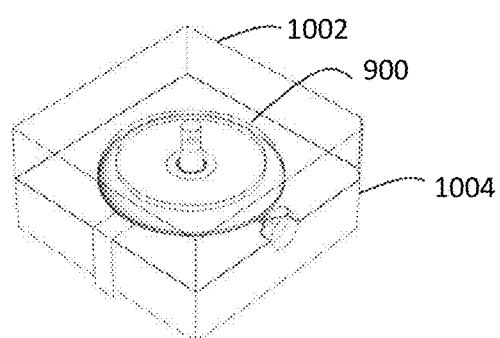
Figure 10D:
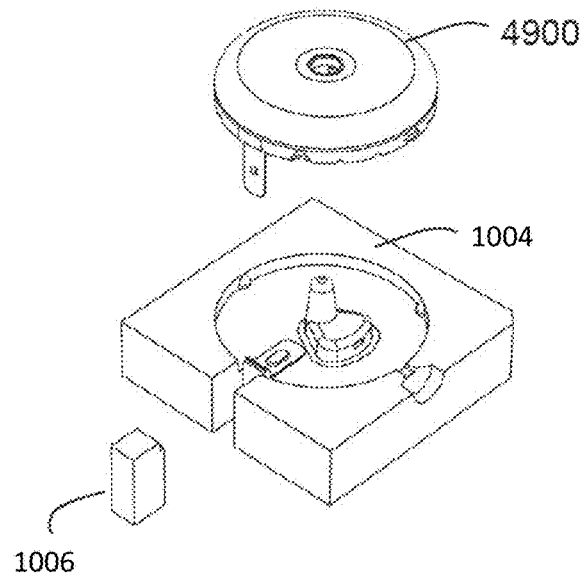

Circuit board 900 is ready for an over-mold process or other sealing method. As illustrated in FIGS. 10A-D, circuit board 900 is first set in a two-piece mold 1002, 1004. A mold slide 1006 is inserted and mold 1002, 1004 is closed as shown in FIG. 10B. As depicted in FIG. 10C, a thermoplastic material is injected into the mold 1002, 1004, encasing circuit board 900. Mold 1002, 1004 is opened and the near-final part ejected as shown in FIG. 10D.

Alternatively, the enclosure of the electronics assembly of sensor control device 102 may include elements snap-fit (or welded/adhered) together as illustrated in the assembly view of FIG. 11A, the as-assembled view of FIG. 11B, and in cross-sectional perspective view of FIG. 11C. An enclosure including a top shell 1102 and a mounting base 1104 can be used to sealably enclose and protect circuit board 900. Top shell 1102 (or whatever portion of the housing is opposite optical sensor 308) is preferably transparent, or semi-transparent, to let light pass therethrough so as to permit the light to be incident upon and activate optical sensor 308 (not shown).

When snap-fit, various interference or snap fit elements (e.g., annular rims 1106) may be provided around the entirety of the periphery of the enclosure or as discrete snap-fit connectors (not shown). Notably, such an approach may benefit from additional O-ring sealing elements to avoid fluid intrusion. Alternatively or additionally, adhesive set at the snap junction(s) may be used to ensure good sealing, especially in connection with continuous annular snap-fit features 1106. As seen in FIG. 11C, a trough 1108 or other features can be provided to ensure that adhesive 1110 that may be squeezed out during assembly is not forced into areas that could interfere with operation or assembly of sensor control device 102. In some embodiments, when top shell 1102 and mounting base 1104 are fit together with a bead of adhesive 1110 in place as shown, trough 1108 not only provides space to capture adhesive 1110 squeezed out but also provides additional surface area for a thicker layer of adhesive 1110 to seal the joint. While the entire top shell 1102 can be adapted to permit the passage of light, in an alternative embodiment only portion 1116 immediately adjacent to optical sensor 308 (not shown) is transparent or semi-transparent (e.g., translucent).

Figure 12A:
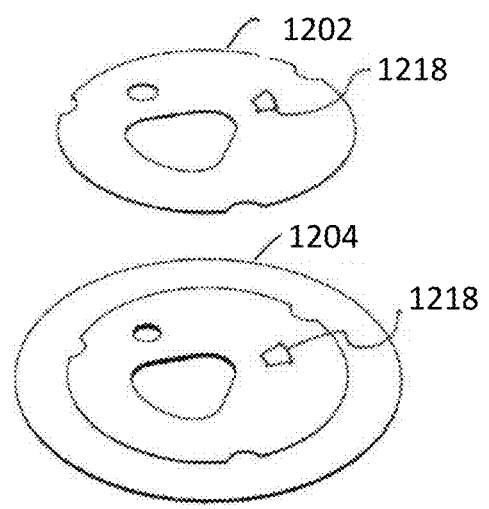
FIGS. 12A-C are assembly views illustrating adhesive backing application in producing a final sensor control device ready for use.
Figure 12B:
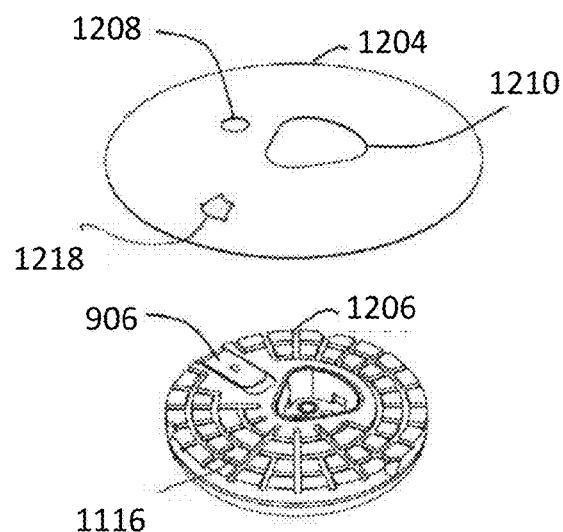
Figure 12C:
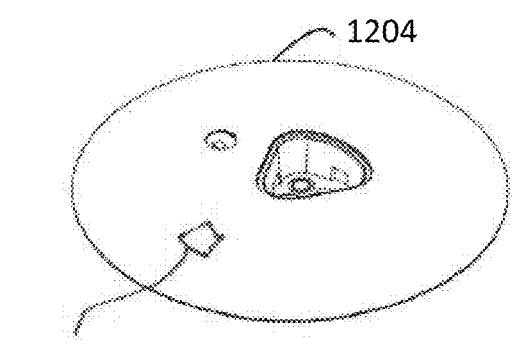

However constructed, final assembly of the electronics assembly of sensor control device 102 involves adhesive patch installation. An exemplary approach is illustrated in FIGS. 12A-C. First, a double-sided adhesive patch 1204 has the inner liner 1202 removed. This exposed adhesive is set over a sensor control device body 1206 (with the temperature sensor 906 folded to seat within a complementary pocket) and adhered with a first window 1208 aligned for temperature sensing, a second window 1210 for sensor assembly receipt, and a third window 1218 aligned with the portion 1116 of shell 1102 immediately adjacent to optical sensor 308 (not shown). The surface of sensor control device 102 facing the user is substantially covered with adhesive except for the aforementioned windows. As such, it is ready for placement in an applicator assembly upon removal of the outer release liner, or alternatively ready for placement in a container with or without the outer liner in place, depending on the presence or absence of any liner-puller features provided therein.

The surface of sensor control device 102 on which window 1218 is located (as shown in FIG. 12C) faces the end cap when the applicator is in its sterile and packaged state. Thus, removal of the end cap immediately exposes window 1218 to the ambient light, causing initialization or activation of sensor control device 102 with little or no extra effort or steps by the user.

Example Embodiments for Changing the Power State Using Wireless Transmissions

Additional embodiments that can be used to activate sensor control device 102, establish communication with sensor control device 102, and/or reestablish communication with sensor control device 102 (e.g., after a prior communication session has ended) are set forth here. These embodiments involve the sending of one or more RF transmissions from reader device 120 to sensor control device 102. In some embodiments, the RF transmissions are sent according to a Bluetooth protocol in the RF band from about 2400 to 2480 Megahertz (Mhz) (or 2.4 to 2.48 Gigahertz (Ghz)), while in other embodiments communications made according to NFC protocols and other protocols and frequency bands can also be utilized.

As already mentioned, sensor control device 102 is provided to the user in a powered-off (or power-off, or deactivated) state where the circuitry of sensor control device 102 consumes little, if any, current from power source 210. Sensor control device 102 can be activated such that it changes state from this powered-off (or storage) state to a second state that consumes relatively higher power.

If in the storage state, the second state may be a normal operation state. If in a fully deactivated powered-off state, the second state may be characterized as a low-power state that is used to conduct low-power monitoring for wireless signals or transmissions coming from reader device 120. These transmissions can advertise the availability of reader device 120 to establish a communication session with sensor control device 102. The transmission(s) can be used to activate sensor control device 102. This low-power state can allow sensor control device 102 to operate for a relatively long period of time while device 102 awaits the receipt of a wireless transmission from reader device 120.

Once sensor control device 102 receives one or more wireless transmissions from reader device 120 that indicate that the user is ready to begin normal usage of sensor control device 102 (e.g., the collection and transmission of sensed analyte data), then sensor control device 102 can optionally transition to a third state that consumes even higher power than the first (e.g., fully deactivated) and second states. In this third state, sensor control device 102 can fully establish the communication link with reader device 120, sense analyte levels in the user's bodily fluid, perform some degree of processing on the sensed data, and/or transmit that sensed data to the reader device 120. Continuous operation in this third state will, in most embodiments, last for a predetermined time period, e.g., 14 days.

Of course, in any of the embodiments described herein, it is possible for sensor control device 102 to temporarily enter lower power states to conserve energy even after commencement of normal operation.

Sensor control device 102 can be activated using wireless RF transmissions, e.g., can transition from a powered-off state, or a storage state, to a higher power state, at any time prior to communicating with reader device 120. For example, sensor control device 102 can be wirelessly activated before removal from its packaging, upon removal from its packaging, after removal from its packaging but prior to application to the user's body, upon application to the user's body, or after application to the user's body.

Figure 13:
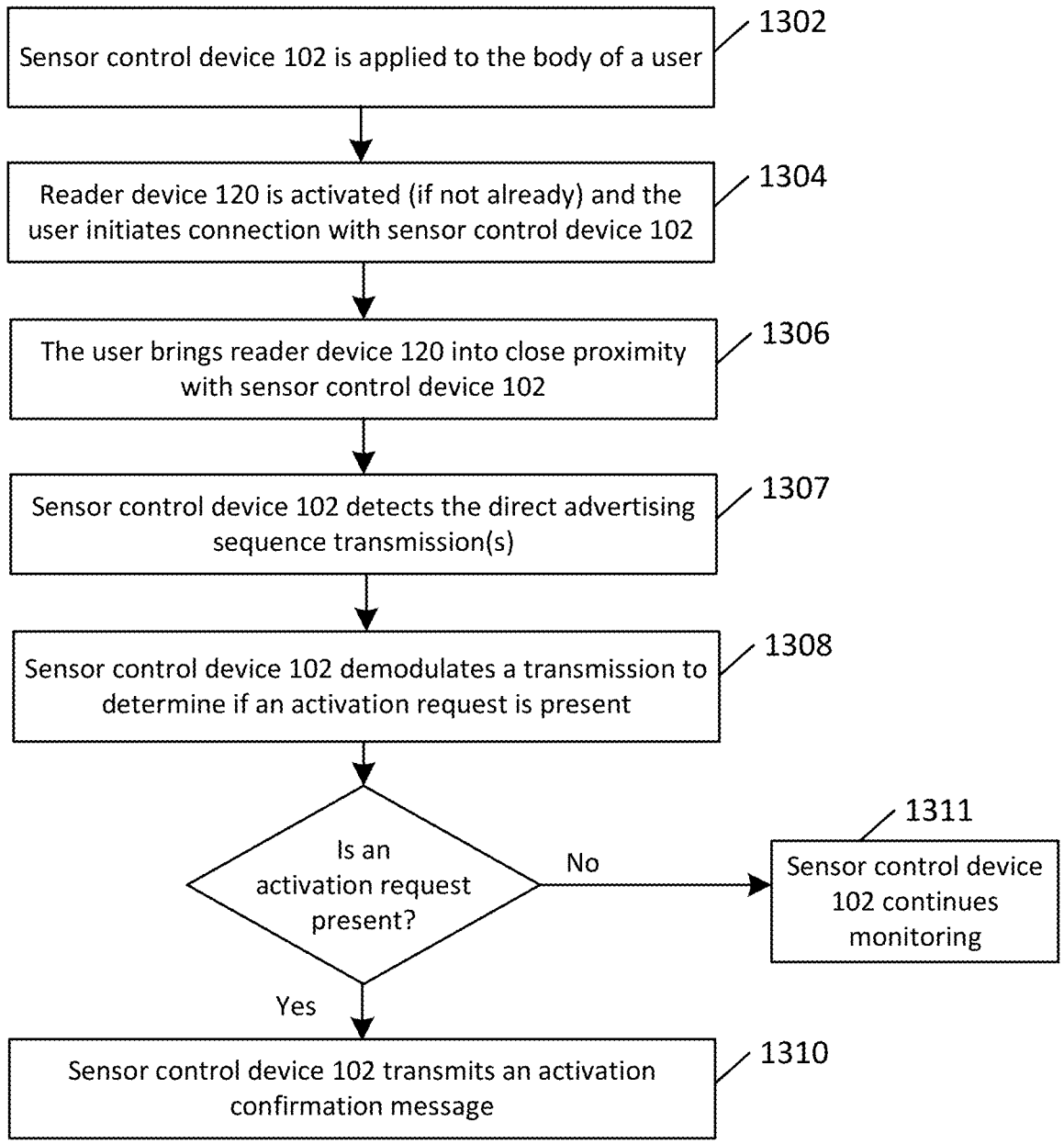
FIGS. 13-14 are block diagrams depicting example embodiments of methods for establishing communication between a sensor control device and a reader device.

FIG. 13 is a block diagram that will be used to describe example embodiments of a method 1300 of establishing communication between sensor control device 102 and reader device 120 using a Bluetooth protocol. These embodiments can also be used to activate sensor control device 102 or otherwise place sensor control device 102 in a higher power state. These embodiments can further be used to re-establish communication between sensor control device 102 and the same or a different reader device 120 with which sensor control device 102 had previously been communicating.

At 1302, sensor control device 102 is applied to the body of a user such that the adhesive patch is satisfactorily adhered to the user's skin with sensor 104 extending into tissue and in contact with bodily fluid (e.g., ISF, dermal fluid, and the like). At this point, it is desirable for sensor control device 102 to monitor for one or more wireless transmissions from reader device 120. Sensor control device 102 can be in either a power-off state or a low-power state, such as a sleep state, that consumes less power than the normal operation state.

If sensor control device 102 is in a powered-off state, then that state should be capable of supplying at least a minimal amount of current to communication circuitry 258 (operating according to the appropriate Bluetooth protocol) to allow monitoring for a wireless transmission from reader device 120. Accordingly, communication circuitry 258 can have a low-power function or state that consumes less power than the normal state of operation, and this low-power state can be used for monitoring for a first wireless transmission from reader device 120.

If the powered-off state is not capable of supplying sufficient current for monitoring for a wireless transmission because, for example, the power source is electrically disconnected, then sensor control device 102 is transitioned from the powered-off state to a low-power state where monitoring is possible. In some embodiments, the powered-off or the low-power state of sensor control device 102 does not permit the transmission of messages in order to save power.

At 1304, reader device 120 is activated (if not already) and the user initiates connection with sensor control device 102 by, for example, selecting an option to do so on the user interface of reader device 120. At 1306, the user brings reader device 120 into close proximity (e.g., less than 6 feet, less than 3 feet, less than 2 feet, less than 1 foot, or less than 6 inches, etc.) with sensor control device 102, if reader device 120 is not already in such a position.

In these embodiments, the initiation of a connection at step 1304 causes reader device 120 to begin sending wireless transmissions according to a Bluetooth protocol. In some of these embodiments, the wireless transmissions are sent in accordance with an advertising regimen of the BTLE protocol, and transmitted at the highest power level allowable by reader device 120. The advertising regimen is a link layer mode of BTLE, and is typically carried out while reader device 120 is in an advertising state by the performance of an advertising event, which can include the sending of one or more advertising request packets on one or more advertising channels (e.g., one, two, or three) of the link layer of the BTLE packet structure (e.g., protocol data unit (PDU) header, PDU payload, CRC). Each packet can be sent on each advertising channel at a specified time interval.

Each advertising packet can contain an advertising request, which is a predetermined string of bits, or bit code, that can be interpreted by sensor control device 102 as a request to initiate the communication session. An example of an advertising request is a packet data unit (PDU) type corresponding to a connectable directed advertising event (ADV_DIRECT_IND). ADV_DIRECT_IND is described in the incorporated Bluetooth specification, version 4.0, as a 0001 code appearing in the 4 most least significant bits (the PDU type) of the PDU header. In certain embodiments, for the connectable directed advertising packet, the time interval between the sending of consecutive requests on the same channel is 3.75 milliseconds (ms) or less, and these repeated transmissions can persist for a predetermined length of time, e.g., as long as about 1.28 seconds (s). If sent on two advertising channels provided by BTLE, the interval between consecutive requests on any channel will be about 1.375 ms or less and, if sent on three channels, the interval will be about 1.25 ms or less.

Other PDUs can be used as well, such as: ADV_IND, which can be a 0000 code corresponding to a connectable undirected event; ADV_NONCONN_IND, which can be a 0010 code corresponding to a non-connectable undirected event; and ADV_SCAN_IND, which can be a 0110 code corresponding to a scannable undirected event.

At 1307, sensor control device 102 detects the advertising message or sequence and, at 1308, demodulates the transmission to determine if an activation request is present. The determination of whether an activation request is present can be performed by processor 256 or communication circuitry 258 (e.g., a BTLE transceiver). If the activation request is present, sensor control device 102 can transmit an activation confirmation message at 1310. The activation confirmation message can be a predetermined bit code that is recognized by reader device 120 as confirmation that sensor control device 102 is ready to establish a connection. For example, the activation confirmation message can be a CONNECT_REQ (0101) or a SCAN_REQ (0011) PDU. In some embodiments, prior to transmitting the activation confirmation message, sensor control device 102 changes into a higher power mode of operation, such as a normal operation state, that enables the use of power to transmit messages. Upon receiving the activation confirmation message, reader device 120 can transition from the advertising state to the connection state according to the BTLE protocol.

If the activation request is not present, then, at 1311, sensor control device 102 can continue to monitor for another transmission sent according to an advertising feature of the BTLE protocol. In some embodiments, sensor control device 102 can wait a predetermined period of time, e.g., 2 to 3 seconds, before monitoring for another transmission.

The user continues to hold reader device 120 in close proximity with sensor control device 102 until reader device 120 indicates, at 1312, that a connection is being established or has been established. This indication can be a visual indication on a display of reader device 120, an audible indication (e.g., a beep, tone, jingle, etc.), a tactile indication (e.g., a vibration or series of vibrations), or any combination thereof. Reader device 120 can provide such an indication upon receiving the activation confirmation message from sensor control device 102. Reader device 120 and sensor control device 102 can then proceed with formally establishing a communication link or pairing and can begin the exchange of analyte data sensed from the body of the user.

Figure 14:
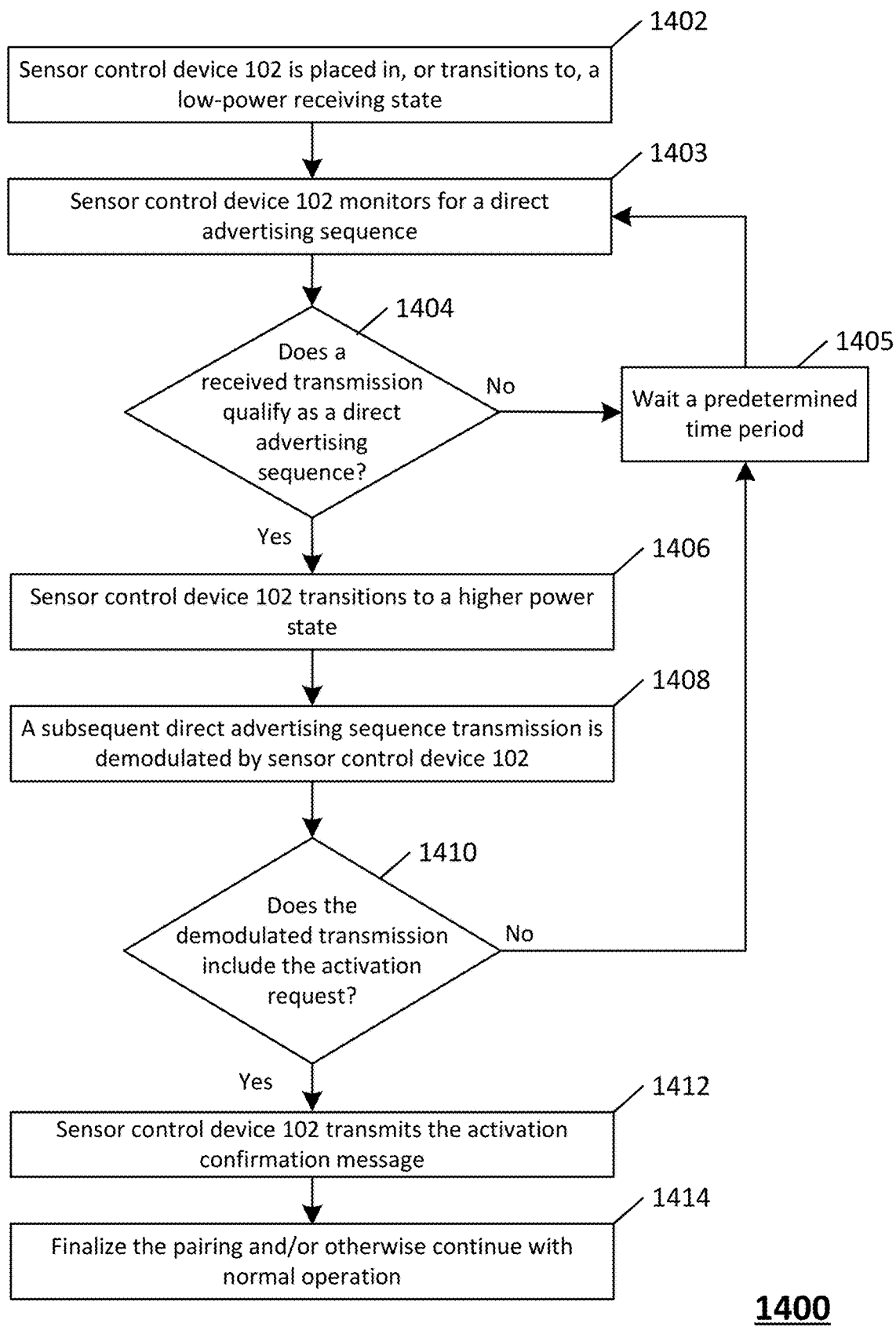

FIG. 14 is a block diagram that will be used to describe additional example embodiments of a method 1400 of establishing a communication link between sensor control device 102 and reader device 120. These embodiments are similar to those embodiments described with respect to FIG. 13, and therefore many of the common aspects will not be repeated, with the attention instead focusing on those aspects that differ.

At 1402, sensor control device 102 is placed in, or transitions to, a low-power receiving mode or state. As already stated herein, sensor control device 102 can be shipped in this state, or can be shipped in a fully powered-off state and transitioned into this state by the user, e.g., manually with a switch or other actuator, or automatically with a photo-sensor or magnetic sensor, etc.

At 1403, sensor control device 102 monitors for a Bluetooth transmission and, if one is received, determines if that transmission qualifies as an advertising message or sequence at 1404. This determination can be accomplished without demodulating the wireless transmission, and can be performed by processor 256 or communication circuitry 258. For example, if a sequence of two or more transmissions are received at the appropriate time interval (e.g., less than or equal to 3.75 ms) and at the appropriate frequency (e.g., approximately 2.4 Ghz), then processor 256 can assume that the transmissions are part of a direct advertising regimen according to the BTLE protocol. If the one or more transmissions do not qualify, then sensor control device 102 returns to monitoring for another wireless transmission, optionally by first waiting the predetermined period of time at 1405.

If the transmission or transmissions do qualify, then at 1406, processor 256 (through its programming) transitions sensor control device 102 to a higher power state that allows for the demodulation of one or more wireless transmissions and the sending of a response. This can be, for example, a normal operation state of sensor control device 102. At 1408, the next, or a subsequent, wireless transmission is demodulated by sensor control device 102 (e.g., by BTLE transceiver 258). At 1410, sensor control device 102 determines if the demodulated transmission includes an activation request. If it does not, then sensor control device 102 can return to the low-power state at 1402 (either before or after waiting an optional predetermined time at 1405), where it can then proceed to monitor for new wireless transmissions.

If the demodulated transmission does include the activation request, then sensor control device 102 transmits the activation confirmation message at 1412. Sensor control device 102 and reader device 120 can then proceed to finalize the pairing and/or otherwise continue with normal operation at 1414.

In another example embodiment, reader device 120 transmits advertising requests as part of a connectable directed advertising event with a maximum power level allowable by the reader device 120, which can be a smart phone. Sensor control device 102 receives one or more of these requests and changes state from a low power (e.g., storage) state to a higher power state (e.g., normal operation). Sensor control device 102 then begins advertising for a connection with reader device 120 according to any advertising regimen in the BTLE protocol (e.g., an advertising regimen that is not a connectable directed advertising event), and reader device 120 can receive the advertising requests and respond accordingly. Thus, in this embodiment, both sensor control device 102 and reader device 120 act as advertisers at some point. Reader device 120 acts as an advertiser to wake up device 102, and device 102 then acts as an advertiser to establish a connection with reader device 120.

Turning now to other embodiments, in some cases, to accomplish a connection of a power source in an electrical manner, another source of power may be required to operate the responsible circuitry. Embodiments of the systems, devices, and methods described herein provide for, among other things, the utilization of the power (or current) harnessed from multiple wireless RF communications, e.g., NFC communications, sent from reader device 120 to sensor control device 102 to drive the responsible connection circuitry. These multiple RF communications provide the power necessary to connect the power source or otherwise cause the source to supply the operating power to sensor electronics 250. In certain embodiments, this can entail harnessing sufficient power to enable processor 256 of sensor control device 102 to demodulate and interpret a wirelessly received transition command that instructs sensor control device 102 to transition from a low-power mode to a higher-power mode, e.g., from an inactive mode to an activate mode. Typically, the greater the efficiency of the sensor control device's power management circuitry 254, the lesser the number of RF communications that are required to successfully transition.

The use of multiple wireless RF communications provides greater power than just a single RF communication of the same type, which may be insufficient. The amount of power that is available in this RF "scavenging" process is dependent on a number of factors such as the antenna efficiency (e.g., tuning), the alignment of the RF fields (distance, position, and plane angle), and the power of the sending communication circuitry (e.g., the transmitter or transceiver) within the reader device.

As mentioned earlier, reader device 120 can be a dedicated-use type device that is designed for the primary (or sole) purpose of interfacing with sensor control device 102. Dedicated-use type reader devices 120 are typically, but not always, manufactured by the same entity that manufactures sensor control device 102. Because the manufacturers have control over the design of dedicated-use reader devices 120, they can be configured to transmit RF communications at a sufficiently high power level that enables sensor control device 102 to transition to a higher-power mode after receiving a minimal number of communications.

In other embodiments, however, reader devices 120 (including some dedicated-use devices) have more limited capabilities and transmit at lower power levels. One example is a multi-function smartphone, where the function of interfacing with sensor control device 102 is an ancillary one only fully implemented by those users that require it. Smartphones are designed to maximize battery life and limit the consumption of power by the secondary circuits such as the NFC communication circuitry that may be used to communicate with sensor control device 102. Due to size constraints, the smartphone may also have a smaller NFC antenna than that of a dedicated-use device. As a result, the amount of power that can be scavenged from each RF communication is limited, often severely. The systems, devices, and methods described herein, while not limited to such, are particularly suited for smartphones and other reader devices that send RF communications at a relatively low power.

Figure 15:
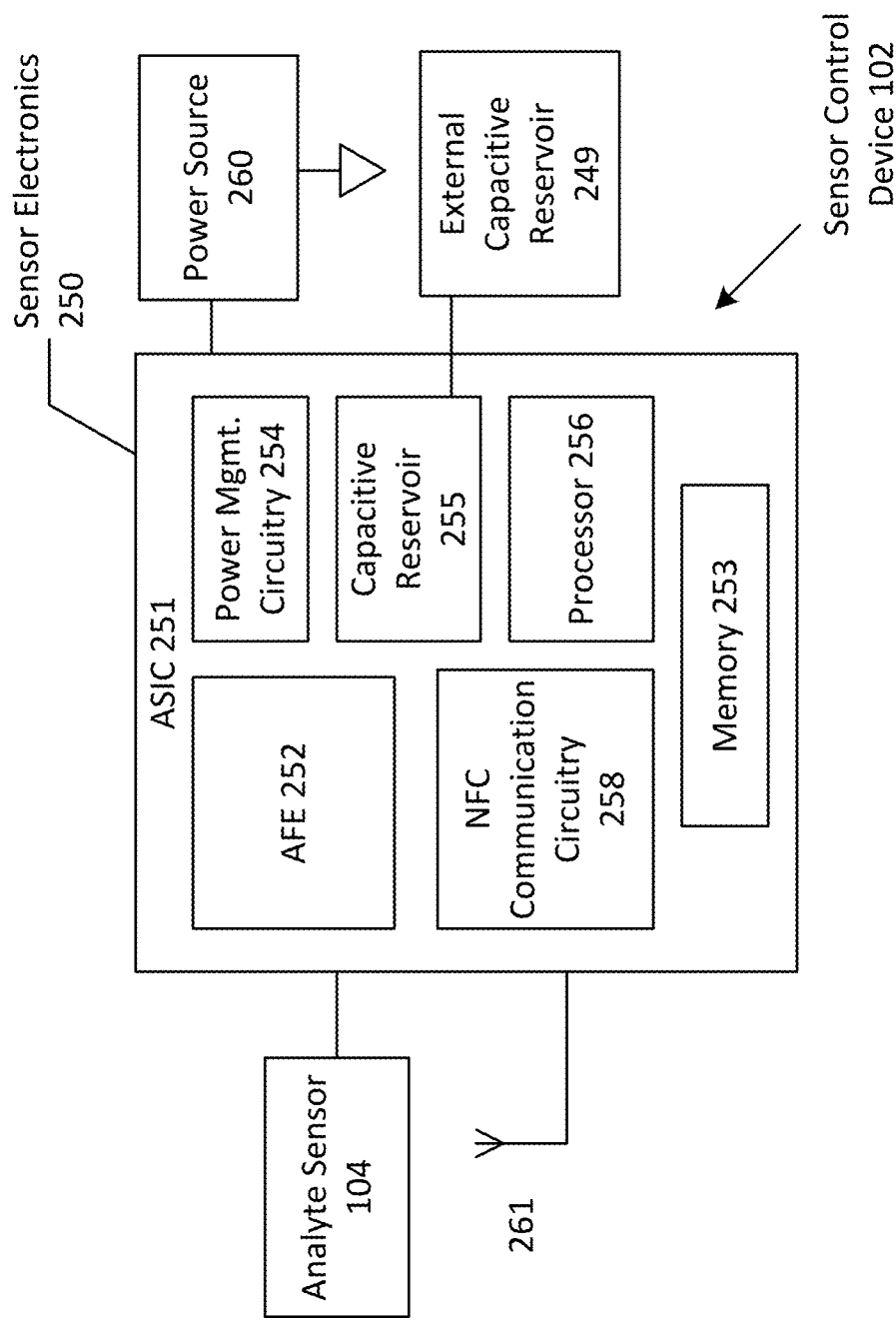
FIG. 15 is a block diagram depicting another example embodiment of a sensor control device.

FIG. 15 depicts an example embodiment of sensor control device 102 adapted to harness power from received NFC communications. The embodiment here is similar to that described with respect to FIG. 2B, except that also associated with sensor electronics 250 is an internal capacitive reservoir 255 and an external capacitive reservoir 249 for storing the charge drawn from the received wireless communications. The features of this embodiment can also be applied to a configuration such as that described with respect to FIG. 2C. Internal reservoir 255 can be used alone, as can external reservoir 249, or a combination of the two reservoirs 249 and 255 can be used as shown. Capacitive reservoirs 249 and 255 can include one or more capacitors electrically coupled with processor 256, communication circuitry 258 (adapted to send and receive NFC communications), and power management circuitry 254. Multiple capacitors present within reservoirs 249 and 255 can be arranged in parallel fashion to maximize the charge storage capability.

Figure 16:
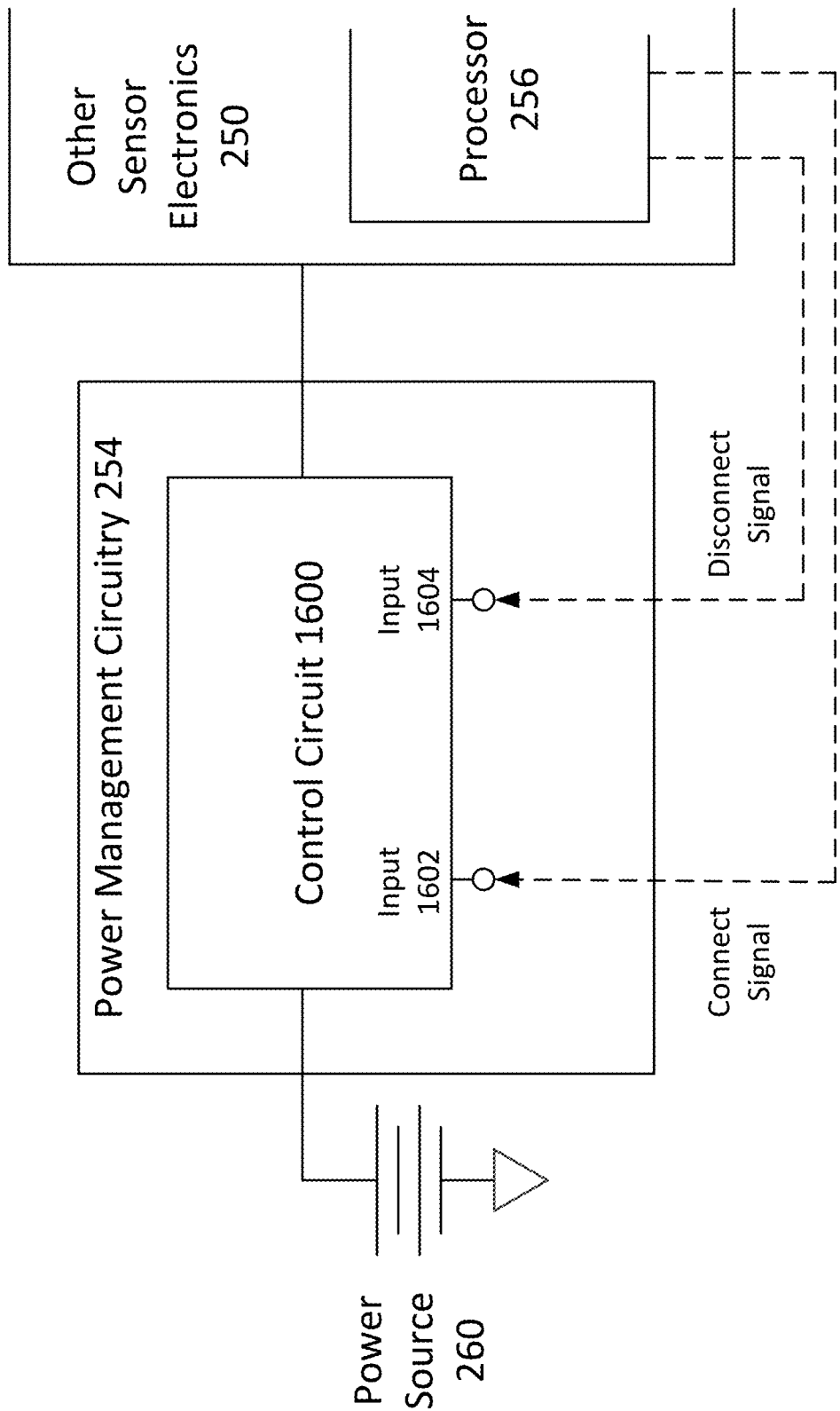
FIG. 16 is a block diagram depicting an example embodiment of power management circuitry.

Power management circuitry 254 can perform voltage level monitoring of power source 260, can monitor the level of charge stored within capacitive reservoirs 249 and 255, and can also include control circuitry for controlling whether power source 260 is supplying the operating power to the remainder of sensor electronics 250. FIG. 16 is a block diagram depicting an example embodiment of a low leakage control circuit 1600 that includes at least one transistor arranged to act as a switch determining whether power source 260 is electrically connected to the remaining electronics 250 (such that the operating power can be supplied) or electrically disconnected from the remaining electronics 250 (such as when sensor control device 102 is in a low-power mode). Examples of such control circuits 1600 are described in co-pending U.S. Provisional Application No. 61/899,983, filed Nov. 5, 2013, which is incorporated by reference herein in its entirety for all purposes.

Control circuit 1600 can be responsive to a first control signal at an input 1602 (e.g., a connection command) that causes control circuit 1600 to connect power source 260 to the remaining sensor electronics 250. Control circuit 1600 can also be responsive to a second control signal at an input 1604 (e.g., a disconnection command) that causes control circuit 1600 to disconnect power source 260 from the remaining sensor electronics 250. These control signals can be generated by power management circuitry 254 or processor 256 using the power stored in capacitive reservoirs 249 and/or 255.

Figure 17A:
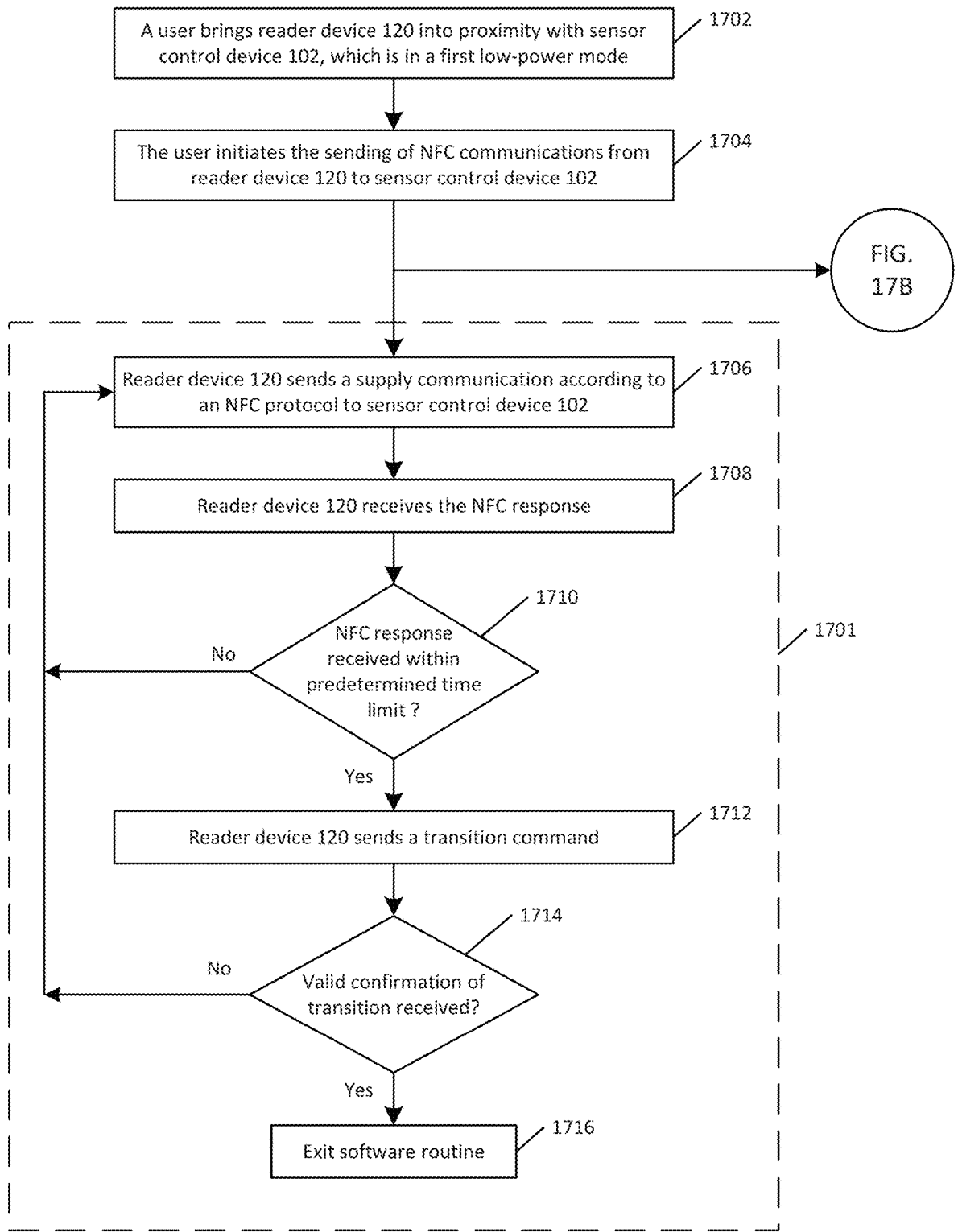
FIGS. 17A-B are flow diagrams depicting an example embodiment of a method of supply power to a sensor control device with successive RF communications sent by a reader device.

Turning now to detailed description of the RF power transfer techniques, FIG. 17AB are flow diagrams depicting an example embodiment of a method 400 of supplying power to sensor control device 102 with wireless communications sent by reader device 120 according to an NFC protocol.

NFC is a technique for establishing radio communication between devices by touching them or bringing them into close proximity to each other (by way of a non-limiting example, any spaced relation up to about 1.5 meters (m)). NFC devices typically send communications by generating a magnetic field with an inductive antenna at a frequency around 13.56 MHz. This magnetic field induces current in a similar inductive antenna in the receiving NFC device, which can then be decoded to interpret the contents of the communication. NFC devices can be "active" or "passive" devices. Active devices typically include their own power source for generating voltage or current used to send NFC requests and responses. Passive devices typically do not include their own power source and respond to a received communication by using power scavenged from that communication.

The term "NFC" applies to a number of protocols (or standards) that set forth operating parameters, modulation schemes, coding, transfer speeds, frame format, and command definitions for NFC devices. The following is a non-exhaustive list of examples of these protocols, each of which (along with all of its sub-parts) is incorporated by reference herein in its entirety for all purposes: ECMA-340, ECMA-352, ISO/IEC 14443, ISO/IEC 15693, ISO/IEC 18000-3, ISO/IEC 18092, and ISO/IEC 21481.

The embodiments described herein can utilize any of the aforementioned NFC features and can utilize any NFC protocol for supplying power across link 140 regardless of whether that protocol is contained in the aforementioned list or otherwise in existence at the time of this filing. Communication protocols other than NFC can also be used for supplying power across link 140. For example, with supplemental power harnessing circuitry, Wi-Fi transmissions could be used to transfer power of link 140 to sensor control device 102.

Now referring back to FIG. 17A, at 1702 a user brings reader device 120 into proximity with sensor control device 102, which is in a first low-power mode. At 1704, the user initiates the sending of NFC communications from reader device 120 to sensor control device 102. This portion of the procedure can occur in a variety of settings. In one example, the user can be activating sensor control device 102 for the first time, before or after applying device 102 to the user's body, in which case sensor control device 102 may be in a power-off mode or storage mode. The user can select an option on reader device 120 to activate sensor control device 102 to commence that device's initialization for purposes of monitoring the user's analyte levels. This instruction in turn initiates the sending of the NFC communications from reader device 120.

In another example, sensor control device 102 may have already been activated and applied to the user's body, and has instead entered a power conservation or sleep mode that disconnects power source 260 from a portion of sensor electronics 250 not directly responsible for analyte monitoring. In such an example the user may select an option to perform a scan of sensor control device 102 and retrieve the user's most current analyte data, which in turn initiates the sending of the NFC communications to "wake-up" sensor control device 102.

In FIG. 17A, the actions taken by reader device 120 are shown within box 1701. The corresponding actions taken by sensor control device 102 are shown within box 1703 of FIG. 17B. In both cases, all actions can be performed in part using the respective device's processors. At 1706 of FIG. 17A, reader device 120 sends a supply communication according to an NFC protocol to sensor control device 102. The supply communication, which is discussed in more detail below, is selected to supply an amount of power to sensor control device 102 that is greater than the amount of power consumed by sensor control device 102 to interpret the supply communication and take the action programmed as a response to the supply command.

Sensor control device 102 receives the supply communication at 1730 (FIG. 17B) and demodulates and reads the message contained therein at 1731. At 1732, sensor control device 102 determines if the communication contains a transition command, which it does not at this point. Recognizing that the message contains a supply command, sensor control device 102 takes the appropriate action (if any) requested by the supply command and sends an NFC response to the command at 1733. Sensor control device 102 stores the excess charge (or power) from the received communication in capacitive reservoirs 249 and/or 255 at 1734. Step 1734 can occur concurrently with step 1733 or later (as shown). The storage of charge in reservoirs 249 and 255 can occur only upon the receipt of a valid supply command if desired (e.g., if charge can be harnessed from certain random noise then that charge would not automatically be stored in reservoirs 249 and 255).

Reader device 120 receives the NFC response at 1708 (FIG. 17A) and determines whether it was received within a predetermined or allotted time limit (or time window) at 1710. If the NFC response was not received within the predetermined time limit, then reader device 120 will revert to step 1706 and send another supply command to sensor control device 102. This process can repeat until a valid NFC response is received within the predetermined time limit or until reader device 120 has sent a maximum number of supply commands or otherwise reached a maximum time limit for the process.

If a valid NFC response is received within the predetermined time limit, then reader device 120 sends a transition command at 1712. The transition command instructs sensor control device 102 to cause power source 260 to supply the operating power to sensor electronics 250. This can entail instructing sensor control device 102 to transition from the low-power mode to a higher power mode. The transition command can be an "activation command" that instructs sensor control device 102 to activate and began an initialization process to ready itself for use in collecting analyte data.

Referring back to FIG. 17B, sensor control device 102 receives the communication containing the transition command at 1730 and demodulates and reads it at 1731. At 1732, sensor control device 102 determines if the communication contains a transition command, which it does at this point. Recognizing that it is a transition command, sensor control device 102 can proceed in various manners. In the example depicted here, sensor control device 102 determines whether sufficient charge has been collected from the one or more supply commands at 1735. Power management circuitry 254 can generate a flag indicating whether or not sufficient charge has been collected and communicate it to processor 256, which can sense the flag to arrive at the determination of step 1735. If sufficient charge is present, then, at 1736, sensor control device 102 can use that charge to cause power supply 260 to supply the operating power, e.g., by outputting a connection command from processor 256 to control circuit 1600 that causes the connection of supply 260 to the remainder of sensor electronics 250. Sensor control device 102 can also send a confirmation to reader device 120 that it has successfully executed the transition command. If sufficient charge is not present, then, at 1738, sensor control device 102 can send an NFC response to reader device 120 that it cannot execute the transition command. Alternatively, sensor control device 102 can take no action to conserve power.

In another example, after recognizing that a transition command has been received, sensor control device 102 can forego determining whether sufficient charge is present (step 1735) and attempt to execute the command directly. Sensor control device 102 will either succeed or not depending on whether sufficient charge has been collected. Sensor control device 102 can then optionally perform the appropriate action described with respect to steps 1736 and 1738.

Reader device 120 monitors for receipt of confirmation that the transition command was executed at 1714 (FIG. 17A). If a valid confirmation was received, then reader device 120 can exit the routine at 1716, having successfully supplied the requisite power to sensor control device 102. If no confirmation was received, or a negative indication was received, reader device 120 reverts to sending supply commands at 1706 and the process can repeat as many times as permitted by the software.

As mentioned, the communication containing the supply command is selected to result in a net power gain for sensor control device 102, i.e., the power required to read and react to the communication is less than the power conveyed to sensor control device 102 by its receipt. The action that the command instructs sensor control device 102 to take may not be a needed one at the point in time that it is sent by reader device 120. In other words, the command's execution may be considered to be a negligible artifact of this power supply technique. One example of a supply command is the inventory command set forth in ISO 15693-3, which instructs sensor control device 102 to perform the anti-collision sequence of that protocol. In ISO 15693, each NFC request contains flags, a command code, mandatory and optional parameter fields depending on the command, application data fields, and a cyclic redundancy check (CRC), while an NFC response contains similar fields but omits the command code. Sensor control device 102 can be designed to achieve net power gains from the other commands described in ISO 15693-3, which are reiterated in Table 1 below.

TABLE 1

| Command Code | Type | Function |
| --- | --- | --- |
| 01 | Mandatory | Inventory |
| 02 | Mandatory | Stay Quiet |
| 20 | Optional | Read Single Block |
| 21 | Optional | Write Single Block |
| 22 | Optional | Lock Block |
| 23 | Optional | Read Multiple Blocks |
| 24 | Optional | Write Multiple Blocks |
| 25 | Optional | Select |
| 26 | Optional | Reset to Ready |
| 27 | Optional | Write AFI |
| 28 | Optional | Lock AFI |
| 29 | Optional | Write DSFID |
| 2A | Optional | Lock DSFID |
| 2B | Optional | Get System Information |
| 2C | Optional | Get Multiple Block Security Status |

Figure 17B:
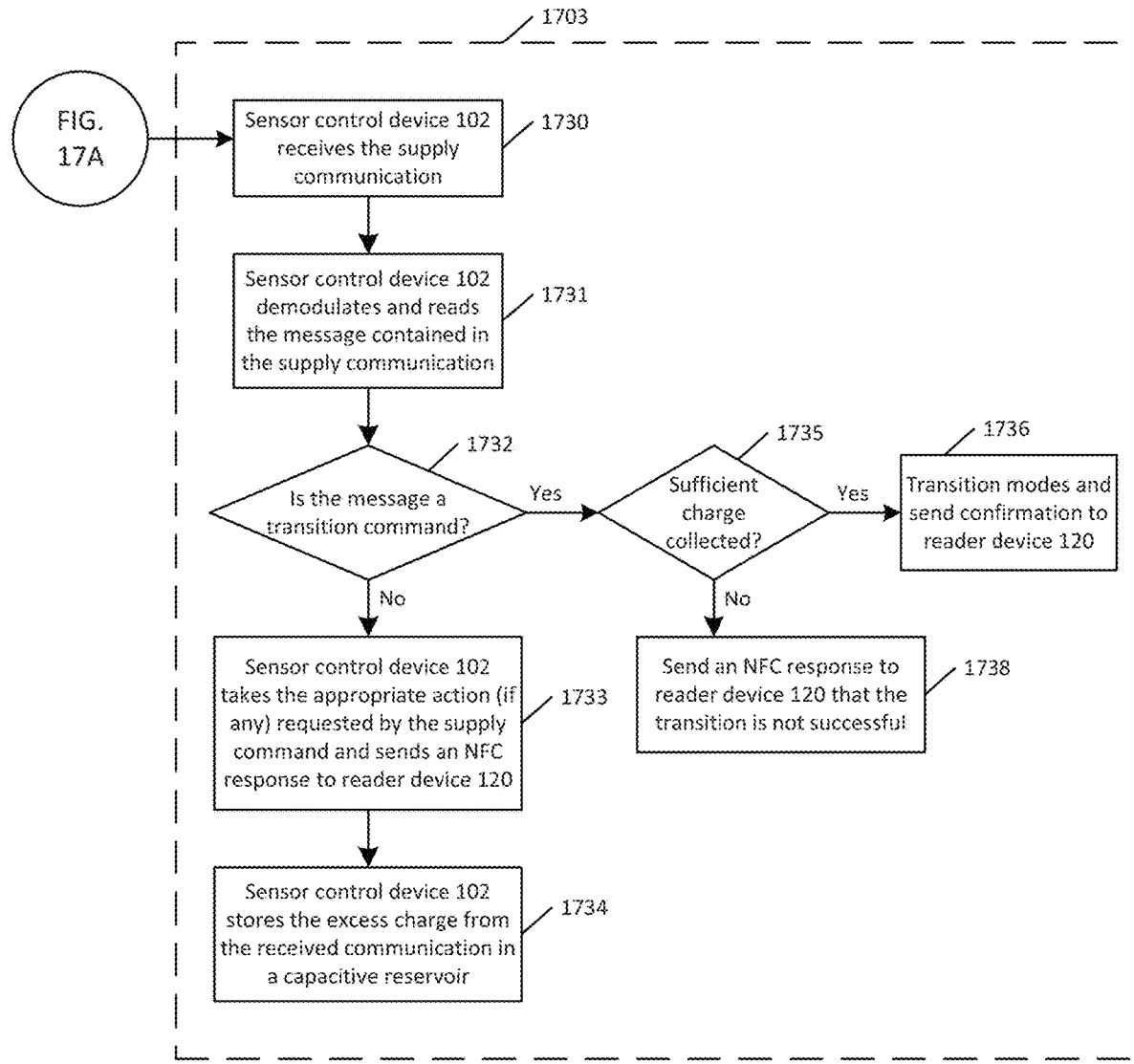

In the embodiment of method 1700 described with respect to FIGS. 17A-B, reader device 120 is permitted to send a large number of successive supply commands prior to sending the transition command. It is not required that these supply commands be identical, as any combination of commands can be used, including commands that do not result in a net power gain for sensor control device 102 (although the use of those commands should be minimized to obtain the maximum power supplying effect). In one embodiment the supply commands are a majority of the commands that are sent. The supply commands can be sent at the outset and followed by one or more non-supply commands, or a number of non-supply commands can be sent initially before the supply commands, or the commands can be interleaved in any desired combination. Likewise, the transition command can be followed by other commands including additional supply commands.

Furthermore, reader device 120 need not monitor for an NFC response to each supply command and can instead be programmed to send a specific number of supply commands in rapid succession. Reader device 120 can follow with a transition command and monitor for a successful response. The sending of the supply commands in rapid succession increases the likelihood of supplying sufficient power to sensor control device 102 while minimizing the length of the process, as it is desirable to avoid significant delays that are perceptible to the user. In one non-limiting example that was experimentally performed, four supply commands are sent at intervening intervals of 130 milliseconds (ms) with a transition command sent every 600 ms until confirmation of success is received. In another non-limiting example that was also experimentally performed, ten supply commands were sent in succession followed by a transition command. It was experimentally determined that ten supply commands provide sufficient margin to supply power across a wide range of commercially available smartphones under the most common conditions of alignment and separation forming the NFC link. Other examples include the sending of X supply commands prior to the sending of a transition command, where X is 2, 3, 5, 6, 7, 8, 9, 11, 12, and so forth, wherein each cycle of sending supply commands followed by a transition command can be repeated X times or as many times as desired until the desired transition is carried out.

Figure 18:
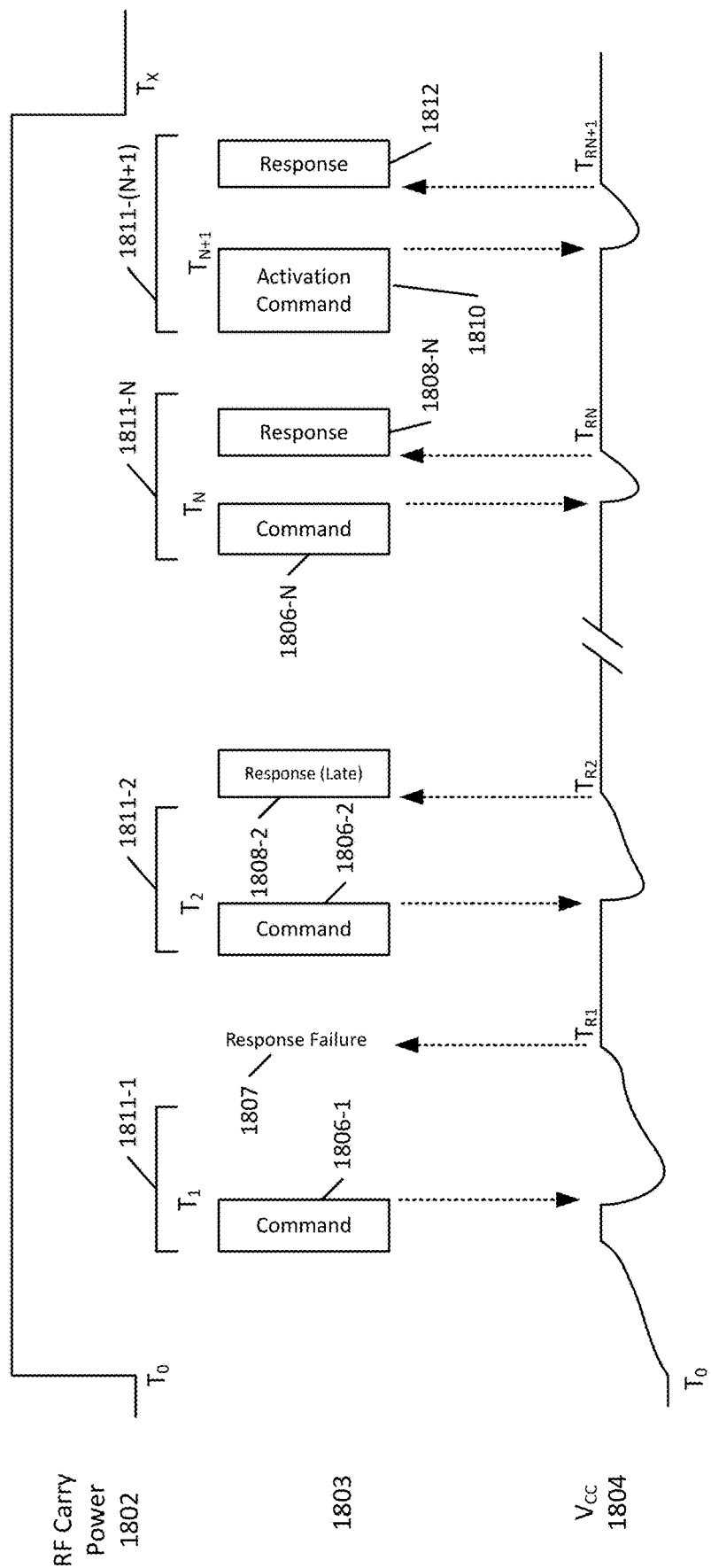
FIG. 18 is a conceptual timing diagram depicting power levels of a reader device and sensor control device, and various communications and communication attempts between those devices.

FIG. 18 is a conceptual diagram depicting an example situation where method 1700 is implemented. Several different parameters are depicted here in timed relationship to each other. The upper portion 1802 depicts the activation of the RF carry power for reader device 120. The RF carry power here is a general representation of the energy propagated by reader device 120 in the transmission of the carrier wavelengths over link 140. In accordance with the NFC protocol, supply of the RF carry power over link 140 can continue so long as the transmission of NFC commands (e.g., NFC Requests) is taking place. Supply of the RF carry power is initiated at time $T_0$ and ceased at time $T_X$. The middle portion 1803 depicts the sending of the NFC communications by both reader device 120 and sensor control device 102. The lower portion 1804 depicts the voltage $V_{CC}$ available to sensor control device 102 upon receiving and reacting to each command sent by reader device 120.

Upon initiation of the RF carry power at $T_0$, reader device 120 begins sending commands and $V_{CC}$ begins to rise from a zero (or near-zero) value to a regulated maximum voltage. A communication containing supply command 1806-1 is received by sensor control device 102 at $T_1$. Sensor control device 102 demodulates the communication, interprets command 1806-1, and attempts to generate and send a response within predetermined time limit 1811-1. But as indicated by the precipitous drop in $V_{CC}$ that occurs after receipt of supply command 1806-1, sensor control device 102 has insufficient power to send any response, as indicated by the response failure 1807 at $T_{R1}$.

At $T_2$, reader device 120 sends a second supply command 1806-2. Here, sensor control device 102 again experiences a drop in $V_{CC}$, although this drop is of less magnitude and duration because of the partial charging of reservoirs 249 and 255, and sensor control device 102 is able to send a delayed response 1808-2 at $T_{R2}$. Because this delayed response 1808-2 is not received by reader device 120 within the predetermined time limit 1811-2, reader device 120 proceeds to send additional supply commands.

At $T_N$, an $N_{th}$ supply command 1806-N is received by sensor control device 102. The $V_{CC}$ drop here is of even less magnitude and less duration than the ones occurring at $T_1$ and $T_2$, and at $T_{RN}$ sensor control device 102 sends a valid response 1808-N within the predetermined time limit 1811-N.

Upon confirming this valid response 1808-N, reader device 120 sends a transition command 1810 that is received by sensor control device 102 at $T_{N+1}$. Sufficient charge is present to permit sensor control device 102 to perform a successful mode transition and sensor control device 102 sends a response 1812 with confirmation of the transition at $T_{RN+1}$. Because of the higher power requirement to respond to transition command 1810, the $V_{CC}$ drop is greater and longer than that experienced responding to the preceding supply command 1806-N.

Figure 19:
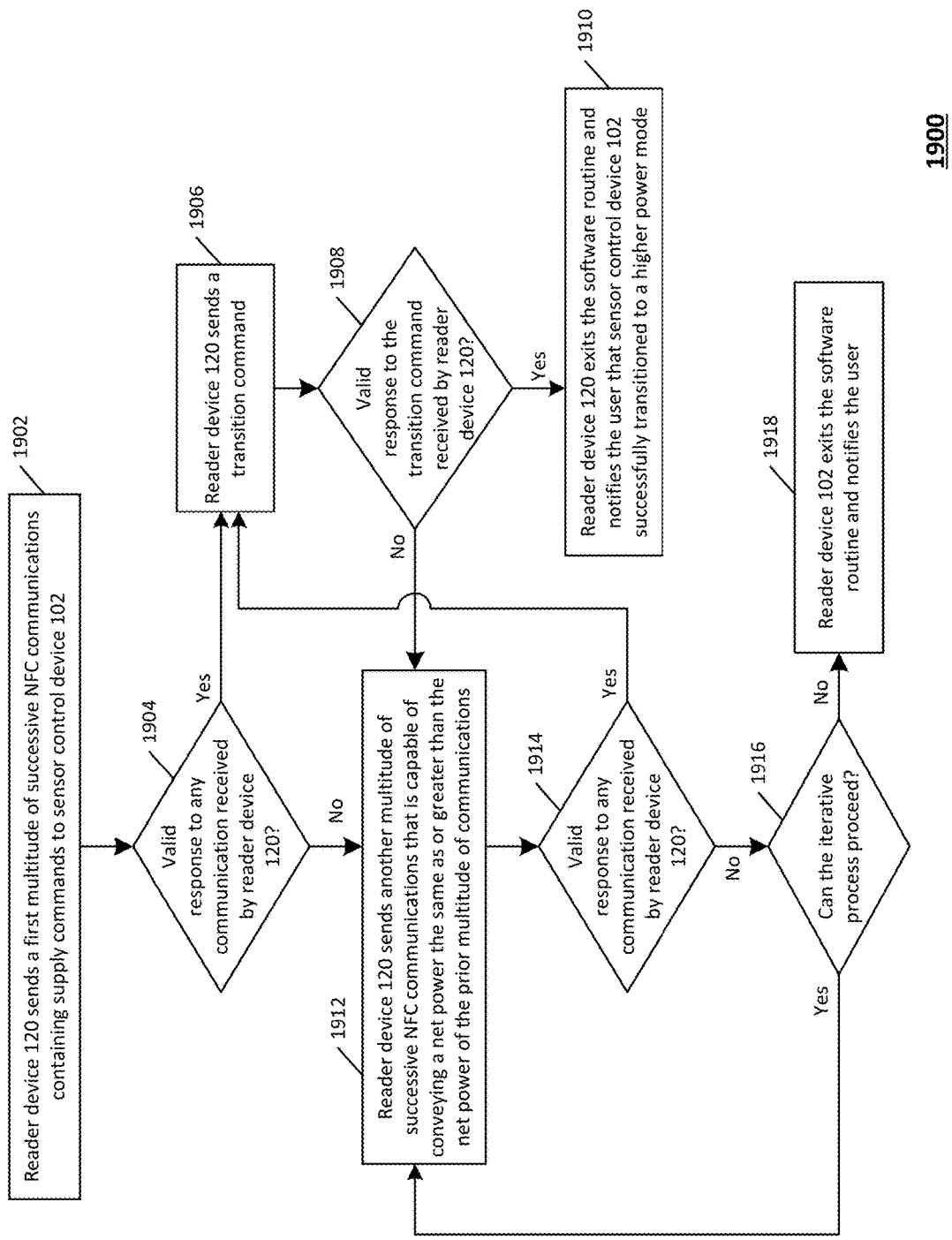
FIG. 19 is a flow diagram depicting an example embodiment of a method of adaptively supplying power to a sensor control device.

Also provided herein are adaptive techniques that can adjust the amount of power supply to sensor control device 102 based upon one or more failures to transition device 102 out of a low-power mode. FIG. 19 is a flow diagram depicting an example embodiment of a method 1900 of adaptively supplying power to sensor control device 102.

At 1902, reader device 120 sends a first multitude of successive NFC communications containing supply commands to sensor control device 102. This first multitude of communications is selected so that it is capable of conveying a first net power to sensor control device 102. Every one of the first multitude of communications can contain a supply command, or one of the communications, such as the last communication, can contain a transition command. In this and any embodiment described herein, if the sensor control device 102 can interpret and react to a transition command while maintaining a net power gain, then all supply commands can be transition commands. At 1904, reader device 120 monitors to determine whether a valid response was received from sensor control device 102 to any of the first multitude of communications, or alternatively to any transition command that was sent.

If a valid response was received to one of the supply commands, and no transition command was sent, then reader device 120 sends a transition command at 1906 and determines whether a valid response was received to the transition command at 1908. If a valid response was received then reader device 120 can exit the software routine and optionally notify the user that sensor control device 102 successfully transitioned to a higher power mode (e.g., was activated) at 1910. If no valid response was received to one of the supply commands (see 1904) or if no valid response was received to the transition command (see 1908), then reader device 120 proceeds to 1912, where another multitude of successive NFC communications is sent that is capable of conveying a net power that is the same as or greater than the net power of the multitude of communications that was sent immediately prior, which in this example was the first multitude.

The net power conveyed to sensor control device 102 can be increased in a number of ways. For example, a greater number of communications can be sent over the same time period, or substantially the same time period, as was used with the preceding multitude of communications. Alternatively, the same number of communications can be sent over a shorter time period than was used with the preceding multitude of communications. This approach could be used if sensor control device 102 was susceptible to leakage of the received power. Also, the same number of communications can be sent over the same time period as was used with the first multitude, except each communication can be sent at a higher power. In yet another example, a type of supply command can be used that is different from the supply command in the preceding multitude an effort to adaptively locate the type of supply command that most efficiently transfers power to sensor control device 102. A combination of any two or more of the aforementioned approaches can also be used.

At 1914, reader device 120 determines whether a valid response was received to any of the most recently transmitted multitude of communications, similar to step 1904. If so, then reader device 120 proceeds to 1906 and executes it in a similar fashion to that already described. If no valid response was received at 1914, then reader device 120 proceeds to 1916 and determines if the iterative process can proceed. Factors that can be used in this assessment can include whether reader device 120 is already sending communications at a maximum transmit power, whether a maximum number of attempts has been reached, or whether a maximum duration of time for the entire process has been reached. If the process can proceed then reader device 120 continues to 1912 and sends yet another (in this example a third) multitude of communications capable of conveying an even higher net power. If a maximum has been reached as determined at 1916, then reader device 120 can exit the routine and optionally notify the user at 1918.

Reader device 120, when in the form of a smartphone, can perform the methods described herein under the control of a downloadable software application executed by applications processor 204. The smartphone application can be generic to different smartphone models and can execute an adaptive process like that of method 1900 to determine the optimum combination of supply command timing, supply command type, or number of supply command communications, to supply power to each different smartphone model.

Such an adaptive process could be executed upon installation of the software application, periodically in association with a scan of sensor control device 102, or during a scan as part of a retry process. If sensor control device 102 is already activated, then reader device 120 can send a notification to sensor control device 102 that it is performing the optimization process, at which point sensor control device 102 can scavenge power from the subsequent supply commands and transmit a notification back to reader device 120 as to the amount of power successfully scavenged. Reader device 120 can then attempt different combinations of the aforementioned variables, each time receiving an indication from sensor control device 102 as to the amount of power scavenged. The optimal combination can then be used for accomplishing future mode transitions with that sensor control device 102 or a subsequent one, and can be communicated by reader device 120 back to the manufacturer for future reference, such as over an internet data connection.

Although many of the embodiments described herein are done so in the context of transitioning from a lower power mode to a higher power mode with the aid of a transition command, the power scavenging technique can be used in other contexts as well. For example, these embodiments can be used to prolong the battery life by sending supply commands even after sensor control device 102 has transitioned to the higher power mode (activated). Supply commands can be sent automatically during every communication session between reader device 120 and sensor control device 102, or whenever reader device 120 sends a command known to require greater power consumption than usual. Reader device 120 may be programmed to send supply commands whenever a predetermined subset of NFC commands are transmitted (e.g., an NFC command to perform a scan of the user's analyte level, process the results, and transmit back to reader device 120 is one such command that consumes a large amount of power). Reader device 120 can also send supply commands whenever they are requested by sensor control device 102 during a communication session.

Unless otherwise noted herein, each of the methods steps described in the aforementioned embodiments can be performed by processor 256 or communication circuitry 258 (e.g., a transceiver, or a separate receiver or transmitter). Steps performed by these components can be done at the direction of software programming executed by processor 256.

While many of the embodiments described herein relate to activation of a device, these embodiments are not mutually exclusive. Stated differently, a subject device can include any combination of one or more of the embodiments described herein, including multiple different mechanisms for activating that device.

Generally, embodiments of the present disclosure are used with in vivo systems, devices, and methods for detecting at least one analyte, such as glucose, in body fluid (e.g., transcutaneously, subcutaneously within the ISF or blood, or within the dermal fluid of the dermal layer). In vivo analyte monitoring systems can be differentiated from "in vitro" systems that contact a biological sample outside of the body (or rather "ex vivo") and that typically include a meter device that has a port for receiving an analyte test strip carrying the biological sample of the user, which can be analyzed to determine the user's blood sugar level. Many in vitro systems require a "finger stick" to obtain the biological sample. In vivo analyte monitoring systems, however, can operate without the need for finger stick calibration.

Many embodiments include in vivo analyte sensors arranged so that at least a portion of the sensor is positioned in the body of a user to obtain information about at least one analyte of the body. However, the embodiments described herein can be used with in vivo analyte monitoring systems that incorporate in vitro capability, as well has purely in vitro or ex vivo analyte monitoring systems. Furthermore, the embodiments described herein can be used in systems, devices, and methods outside of the analyte monitoring field, either in other medical device fields, or any other field that requires the supply of power to one device from another.

Sensor Configurations

Analytes that may be monitored with system 100 include, but are not limited to, acetyl choline, amylase, bilirubin, cholesterol, chorionic gonadotropin, glycosylated hemoglobin (HbAlc), creatine kinase (e.g., CK-MB), creatine, creatinine, DNA, fructosamine, glucose, glucose derivatives, glutamine, growth hormones, hormones, ketones, ketone bodies, lactate, oxygen, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In embodiments that monitor more than one analyte, the analytes may be monitored at the same or different times with a single sensor or with a plurality of sensors which may use the same electronics (e.g., simultaneously) or with different electronics of sensor control device 102.

Analyte sensor 104 may include an analyte-responsive enzyme to provide a sensing element. Some analytes, such as oxygen, can be directly electrooxidized or electroreduced on sensor 104, and more specifically at least on a working electrode (not shown) of a sensor 104. Other analytes, such as glucose and lactate, require the presence of at least one electron transfer agent and/or at least one catalyst to facilitate the electrooxidation or electroreduction of the analyte. Catalysts may also be used for those analytes, such as oxygen, that can be directly electrooxidized or electroreduced on the working electrode. For these analytes, each working electrode includes a sensing element proximate to or on a surface of a working electrode. In many embodiments, a sensing element is formed near or on only a small portion of at least a working electrode.

Each sensing element includes one or more components constructed to facilitate the electrochemical oxidation or reduction of the analyte. The sensing element may include, for example, a catalyst to catalyze a reaction of the analyte and produce a response at the working electrode, an electron transfer agent to transfer electrons between the analyte and the working electrode (or other component), or both.

Electron transfer agents that may be employed are electroreducible and electrooxidizable ions or molecules having redox potentials that are a few hundred millivolts above or below the redox potential of the standard calomel electrode (SCE). The electron transfer agent may be organic, organometallic, or inorganic. Examples of organic redox species are quinones and species that in their oxidized state have quinoid structures, such as Nile blue and indophenol. Examples of organometallic redox species are metallocenes including ferrocene. Examples of inorganic redox species are hexacyanoferrate (III), ruthenium hexamine, etc. Additional examples include those described in U.S. Pat. Nos. 6,736,957, 7,501,053 and 7,754,093, the disclosures of each of which are incorporated herein by reference in their entirety.

In certain embodiments, electron transfer agents have structures or charges which prevent or substantially reduce the diffusional loss of the electron transfer agent during the period of time that the sample is being analyzed. For example, electron transfer agents include but are not limited to a redox species, e.g., bound to a polymer which can in turn be disposed on or near the working electrode. The bond between the redox species and the polymer may be covalent, coordinative, or ionic. Although any organic, organometallic or inorganic redox species may be bound to a polymer and used as an electron transfer agent, in certain embodiments the redox species is a transition metal compound or complex, e.g., osmium, ruthenium, iron, and cobalt compounds or complexes. It will be recognized that many redox species described for use with a polymeric component may also be used, without a polymeric component.

Embodiments of polymeric electron transfer agents may contain a redox species covalently bound in a polymeric composition. An example of this type of mediator is poly (vinylferrocene). Another type of electron transfer agent contains an ionically-bound redox species. This type of mediator may include a charged polymer coupled to an oppositely charged redox species. Examples of this type of mediator include a negatively charged polymer coupled to a positively charged redox species such as an osmium or ruthenium polypyridyl cation.

Another example of an ionically-bound mediator is a positively charged polymer including quaternized poly (4-vinyl pyridine) or poly(1-vinyl imidazole) coupled to a negatively charged redox species such as ferricyanide or ferrocyanide. In other embodiments, electron transfer agents include a redox species coordinatively bound to a polymer. For example, the mediator may be formed by coordination of an osmium or cobalt 2,2'-bipyridyl complex to poly(1-vinyl imidazole) or poly(4-vinyl pyridine).

Suitable electron transfer agents are osmium transition metal complexes with one or more ligands, each ligand having a nitrogen-containing heterocycle such as 2,2'-bipyridine, 1,10-phenanthroline, 1-methyl, 2-pyridyl biimidazole, or derivatives thereof. The electron transfer agents may also have one or more ligands covalently bound in a polymer, each ligand having at least one nitrogen-containing heterocycle, such as pyridine, imidazole, or derivatives thereof. One example of an electron transfer agent includes (a) a polymer or copolymer having pyridine or imidazole functional groups and (b) osmium cations complexed with two ligands, each ligand containing 2,2'-bipyridine, 1,10-phenanthroline, or derivatives thereof, the two ligands not necessarily being the same. Some derivatives of 2,2'-bipyridine for complexation with the osmium cation include but are not limited to 4,4'-dimethyl-2,2'-bipyridine and mono-, di-, and polyalkoxy-2,2'-bipyridines, including 4,4'-dimethoxy-2,2'-bipyridine. Derivatives of 1,10-phenanthroline for complexation with the osmium cation include but are not limited to 4,7-dimethyl-1,10-phenanthroline and mono, di-, and polyalkoxy-1,10-phenanthrolines, such as 4,7-dimethoxy-1,10-phenanthroline. Polymers for complexation with the osmium cation include but are not limited to polymers and copolymers of poly(1-vinyl imidazole) (referred to as "PVI") and poly(4-vinyl pyridine) (referred to as "PVP"). Suitable copolymer substituents of poly(1-vinyl imidazole) include acrylonitrile, acrylamide, and substituted or quaternized N-vinyl imidazole, e.g., electron transfer agents with osmium complexed to a polymer or copolymer of poly(l-vinyl imidazole).

Embodiments may employ electron transfer agents having a redox potential ranging from about −200 mV to about +200 mV versus the standard calomel electrode (SCE). The sensing elements may also include a catalyst which is capable of catalyzing a reaction of the analyte. The catalyst may also, in some embodiments, act as an electron transfer agent. One example of a suitable catalyst is an enzyme which catalyzes a reaction of the analyte. For example, a catalyst, including a glucose oxidase, glucose dehydrogenase (e.g., pyrroloquinoline quinone (PQQ), dependent glucose dehydrogenase, flavine adenine dinucleotide (FAD) dependent glucose dehydrogenase, or nicotinamide adenine dinucleotide (NAD) dependent glucose dehydrogenase), may be used when the analyte of interest is glucose. A lactate oxidase or lactate dehydrogenase may be used when the analyte of interest is lactate. Laccase may be used when the analyte of interest is oxygen or when oxygen is generated or consumed in response to a reaction of the analyte.

In certain embodiments, a catalyst may be attached to a polymer, cross linking the catalyst with another electron transfer agent, which, as described above, may be polymeric. A second catalyst may also be used in certain embodiments. This second catalyst may be used to catalyze a reaction of a product compound resulting from the catalyzed reaction of the analyte. The second catalyst may operate with an electron transfer agent to electrolyze the product compound to generate a signal at the working electrode. Alternatively, a second catalyst may be provided in an interferent-eliminating layer to catalyze reactions that remove interferents.

In certain embodiments, the sensor works at a low oxidizing potential, e.g., a potential of about +40 mV vs. Ag/AgCl. These sensing elements use, for example, an osmium (Os)-based mediator constructed for low potential operation. Accordingly, in certain embodiments the sensing elements are redox active components that include: (1) osmium-based mediator molecules that include (bidente) ligands, and (2) glucose oxidase enzyme molecules. These two constituents are combined together in the sensing elements of the sensor.

A number of embodiments of sensor configurations that may be used in system 100 are described in Int'l Publication No. WO 2012/174538, titled "Connectors for Making Connections between Analyte Sensors and Other Devices," and also in U.S. Pat. No. 8,435,682, titled "Biological Fuel Cell and Methods," both of which are incorporated by reference herein in their entirety for all purposes. Particular attention is drawn to paragraphs 121-145 of the '528 Publication, several of which are reproduced herein.

All features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. Express recitation of every possible combination and substitution is overly burdensome, especially given that the permissibility of each and every such combination and substitution will be readily recognized by those of ordinary skill in the art upon reading this description.

In many instances, entities are described herein as being coupled to other entities. It should be understood that the terms "coupled" and "connected" (or any of their forms) are used interchangeably herein and, in both cases, are generic to the direct coupling of two entities (without any non-negligible (e.g., parasitic) intervening entities) and the indirect coupling of two entities (with one or more non-negligible intervening entities). Where entities are shown as being directly coupled together, or described as coupled together without description of any intervening entity, it should be understood that those entities can be indirectly coupled together as well unless the context clearly dictates otherwise.

As used herein and in the appended claims, the singular forms "a", "an", and "the" include plural referents unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. A method of supplying power in an in vivo analyte monitoring environment, comprising:
   receiving, by a sensor control device, power from a plurality of successive wireless communications each comprising digital information in a frame format, wherein the sensor control device comprises:
   a sensor adapted to collect analyte data while inserted in a body of a user;
   analyte monitoring circuitry coupled with the sensor; and
   a power source adapted to supply an operating power to the analyte monitoring circuitry, wherein the power source does not supply the operating power to the analyte monitoring circuitry when the plurality of successive wireless communications is received; and
   using, by the sensor control device, the power from the received plurality of successive wireless communications to transition the sensor control device to a mode in which the power source supplies the operating power to the analyte monitoring circuitry.

2. The method of claim 1, wherein the successive plurality of wireless communications comprises a plurality of Near Field Communication (NFC) supply commands followed by a command for the sensor control device to supply the operating power to the analyte monitoring circuitry.

3. The method of claim 2, wherein a cumulative received power of the plurality of NFC supply commands is greater than a cumulative power used by the sensor control device to read and respond to the plurality of NFC supply commands.

4. The method of claim 3, wherein at least one of the plurality of NFC supply commands is an NFC inventory command.

5. The method of claim 1, wherein a cumulative received power of the plurality of successive wireless communications is greater than a cumulative power used by the sensor control device to react to the plurality of successive wireless communications.

6. The method of claim 1, wherein, for a majority of the plurality of received wireless communications, each comprises information in the form of a command, and wherein a power of each received wireless communication within the majority is greater than a power consumed by the sensor control device to read and respond to each of the plurality of received wireless communications.

7. The method of claim 1, wherein the sensor control device further comprises a control circuit adapted to selectively connect the power source to the analyte monitoring circuitry.

8. The method of claim 7, wherein using, by the sensor control device, power from the received plurality of successive wireless communications to cause the power source to supply the operating power to the analyte monitoring circuitry comprises using power from the received plurality of successive wireless communications to cause the control circuit to connect the power source to the analyte monitoring circuitry.

9. The method of claim 8, wherein the analyte monitoring circuitry comprises a processor, and wherein using power from the received plurality of successive wireless communications to cause the control circuit to connect the power source to the analyte monitoring circuitry comprises:
supplying power from the received plurality of successive wireless communications to the processor; and
outputting a control signal from the processor to the control circuit that causes the control circuit to connect the power source to the analyte monitoring circuitry.

10. The method of claim 9, further comprising:
charging a capacitor of the sensor control device with power from the received plurality of successive wireless communications; and
then using the capacitor to supply power to the processor.

11. An in vivo analyte monitoring system, including a sensor control device that comprises:
communication circuitry adapted to receive power from a plurality of successive wireless communications each comprising information in a digital frame format;
a sensor adapted to collect analyte data while inserted in a body of a user;
analyte monitoring circuitry coupled with the sensor and the communication circuitry; and
a power source adapted to supply an operating power to the analyte monitoring circuitry,
wherein the sensor control device is adapted to receive the plurality of successive wireless communications while in a first mode where the power source does not supply the operating power to the analyte monitoring circuitry, and
wherein the sensor control device is adapted to use the power from the received plurality of successive wireless communications to transition the sensor control device to a second mode in which the power source supplies the operating power to the analyte monitoring circuitry.

12. The system of claim 11, wherein each of the plurality of successive wireless communications comprises a plurality of Near Field Communication (NFC) requests followed by a command for the sensor control device to supply the operating power to the analyte monitoring circuitry.

13. The system of claim 11, wherein the sensor control device comprises a processor adapted to interpret an NFC inventory command within a first one of the successive plurality of wireless communications and adapted to interpret a command for the sensor control device to connect the power source to the analyte monitoring circuitry within a second one of the successive plurality of wireless communications.

14. The system of claim 11, wherein the sensor control device comprises at least one capacitor, and wherein the sensor control device is adapted to store excess power from a cumulative received power of the plurality of successive wireless communications in the at least one capacitor.

15. The system of claim 11, wherein the sensor control device further comprises a control circuit adapted to selectively connect the power source to the analyte monitoring circuitry.

16. The system of claim 15, wherein the power source is not connected to the analyte monitoring circuitry in the first mode, and wherein the sensor control device is adapted to use power from the received plurality of successive wireless communications to cause the control circuit to connect the power source to the analyte monitoring circuitry.

17. The system of claim 16, wherein the sensor control device comprises a processor and the sensor control device is adapted to supply power from the received plurality of successive wireless communications to the processor.

18. The system of claim 17, wherein the processor is adapted to use the supplied power to output a control signal to the control circuit that causes the control circuit to connect the power source to the analyte monitoring circuitry.

19. The system of claim 11, further comprising a reader device, wherein the reader device includes:
communication circuitry adapted to send the plurality of successive wireless communications to the sensor control device and to receive a wireless communication from the sensor control device,
wherein the reader device is programmed to send a wireless transition command to the sensor control device after receipt of the plurality of successive wireless communications.

20. The system of claim 19, wherein the sensor control device is adapted to use power from the received plurality of successive wireless communications to cause connection of the power source to the analyte monitoring circuitry after receipt of the transition command.

* * * * *